(12) United States Patent
Gibson et al.

(10) Patent No.: US 7,902,395 B2
(45) Date of Patent: *Mar. 8, 2011

(54) VERSATILE OXIDATION BYPRODUCT PURGE PROCESS

(75) Inventors: Philip Edward Gibson, Kingsport, TN (US); Kenny Randolph Parker, Afton, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/839,575

(22) Filed: Aug. 16, 2007

(65) Prior Publication Data

US 2008/0039649 A1    Feb. 14, 2008

Related U.S. Application Data

(62) Division of application No. 11/655,395, filed on Jan. 19, 2007.

(60) Provisional application No. 60/777,829, filed on Mar. 1, 2006, provisional application No. 60/777,903, filed on Mar. 1, 2006, provisional application No. 60/777,905, filed on Mar. 1, 2006, provisional application No. 60/777,907, filed on Mar. 1, 2006, provisional application No. 60/777,922, filed on Mar. 1, 2006, provisional application No. 60/778,117, filed on Mar. 1, 2006, provisional application No. 60/778,120, filed on Mar. 1, 2006, provisional application No. 60/778,123, filed on Mar. 1, 2006, provisional application No. 60/778,139, filed on Mar. 1, 2006.

(51) Int. Cl.
*C07C 51/16* (2006.01)

(52) U.S. Cl. .......................... 562/409; 562/412; 562/414
(58) Field of Classification Search .................. None
See application file for complete search history.

(56) References Cited

U.S. PATENT DOCUMENTS

| | | | |
|---|---|---|---|
| 2,964,559 A | 12/1960 | Burney et al. | |
| 3,840,641 A | 10/1974 | Wampflier et al. | |
| 3,873,468 A | 3/1975 | Kobinata et al. | |
| 3,950,409 A | 4/1976 | Yokota et al. | |
| 3,996,271 A | 12/1976 | Yokota et al. | |
| 4,081,464 A | 3/1978 | Marsh et al. | |
| 4,158,738 A | 6/1979 | Scott et al. | |
| 4,185,073 A | 1/1980 | Marsh et al. | |
| 4,219,669 A | 8/1980 | Tsuchiya et al. | |
| 4,298,580 A | 11/1981 | Harper et al. | |

(Continued)

FOREIGN PATENT DOCUMENTS

DE    2131470 A    6/1970

(Continued)

OTHER PUBLICATIONS

USPTO Notice of Allowance dated Jan. 15, 2008 for copending U.S. Appl. No. 10/455,016.

(Continued)

*Primary Examiner* — Karl J Puttlitz
(74) *Attorney, Agent, or Firm* — Steven A. Owen; Bernard J. Graves, Jr.

(57) ABSTRACT

Disclosed is a process and apparatus for treating a purge stream in a carboxylic acid production process. The process employs a purge process that allows for the separation of oxidation byproducts into benzoic acid and non-benzoic acid oxidation byproducts, thus providing flexibility in the treatment and use of such oxidation byproducts.

34 Claims, 6 Drawing Sheets

U.S. PATENT DOCUMENTS

Figure 1:
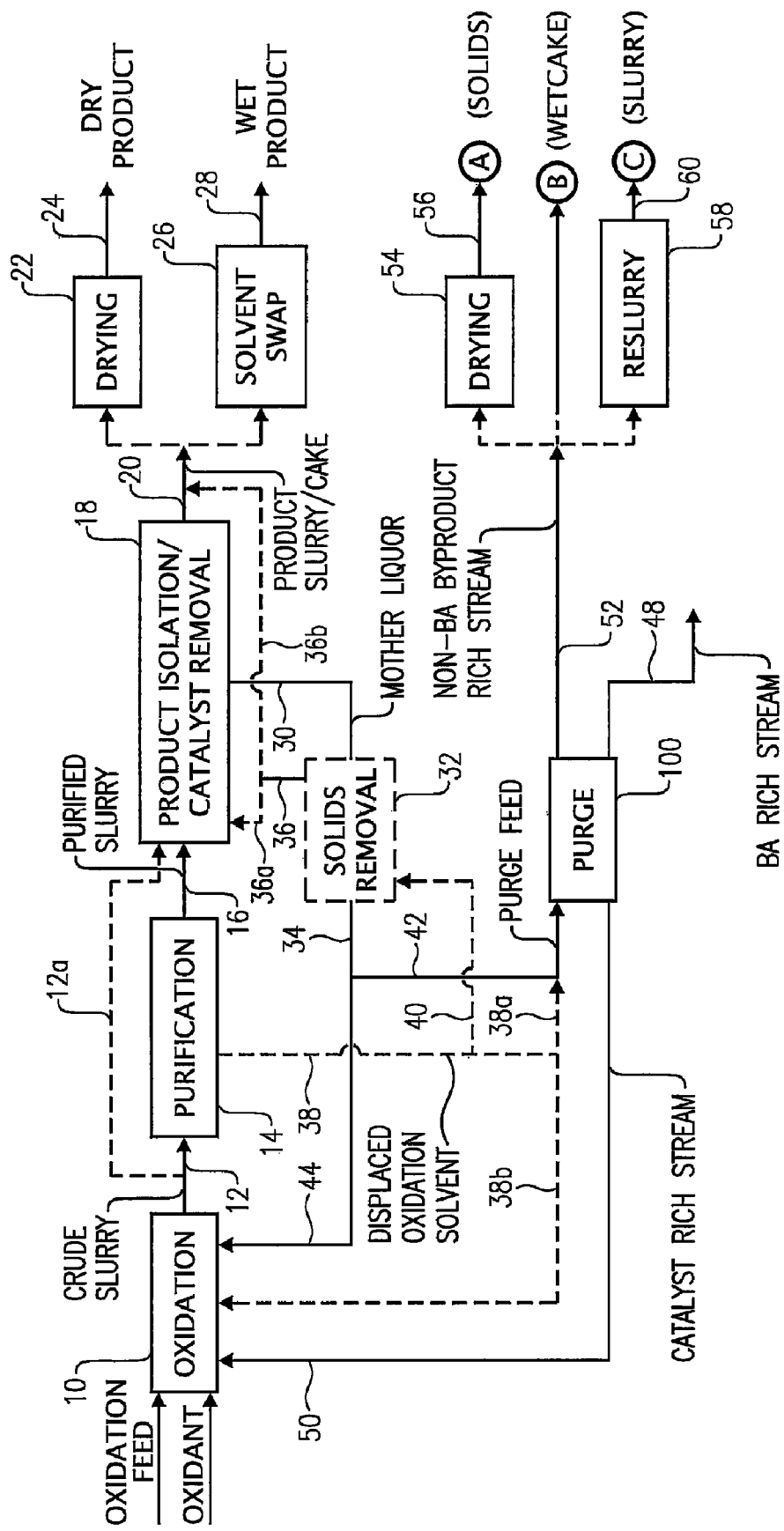

| | | | |
|---|---|---|---|
| 4,330,676 A | 5/1982 | Moxham | |
| 4,356,319 A | 10/1982 | Roffia et al. | |
| 4,769,489 A | 9/1988 | Abrams et al. | |
| 4,892,972 A | 1/1990 | Schroeder et al. | |
| 4,914,230 A | 4/1990 | Abrams et al. | |
| 4,939,297 A * | 7/1990 | Browder et al. | 562/485 |
| 5,200,557 A | 4/1993 | Gee et al. | |
| 5,643,468 A | 7/1997 | Ure | |
| 5,676,847 A | 10/1997 | Yamamoto et al. | |
| 5,705,682 A | 1/1998 | Ohkashi et al. | |
| 5,770,765 A | 6/1998 | Ohkashi | |
| 5,840,965 A | 11/1998 | Turner et al. | |
| 5,916,422 A | 6/1999 | Kimura et al. | |
| 5,955,394 A | 9/1999 | Kelly | |
| 5,973,196 A | 10/1999 | Takano et al. | |
| 5,994,567 A | 11/1999 | Kingsley et al. | |
| 6,054,610 A * | 4/2000 | Lee et al. | 562/487 |
| 6,133,476 A * | 10/2000 | Lin | 562/486 |
| 6,137,001 A | 10/2000 | Broeker et al. | |
| 6,153,790 A | 11/2000 | June et al. | |
| 6,562,997 B2 * | 5/2003 | Sikkenga et al. | 562/413 |
| 7,074,954 B2 | 7/2006 | Sheppard et al. | |
| 7,132,566 B2 | 11/2006 | Sumner et al. | |
| 7,273,559 B2 | 9/2007 | Gibson et al. | |
| 7,291,270 B2 | 11/2007 | Gibson et al. | |
| 7,381,386 B2 * | 6/2008 | Lin et al. | 423/49 |
| 2001/0041811 A1 * | 11/2001 | Sikkenga et al. | 562/416 |
| 2002/0016500 A1 | 2/2002 | Matsumoto et al. | |
| 2002/0193630 A1 | 12/2002 | Lin et al. | |
| 2004/0225148 A1 * | 11/2004 | Isogai et al. | 562/412 |
| 2004/0244536 A1 | 12/2004 | Lin | |
| 2004/0245176 A1 | 12/2004 | Parker et al. | |
| 2004/0249207 A1 | 12/2004 | Lin et al. | |
| 2004/0249208 A1 | 12/2004 | Lin et al. | |
| 2007/0205153 A1 * | 9/2007 | Parker et al. | 210/634 |
| 2007/0208195 A1 * | 9/2007 | Gibson et al. | 562/410 |
| 2007/0208196 A1 * | 9/2007 | Parker et al. | 562/485 |
| 2007/0208197 A1 * | 9/2007 | Gibson et al. | 562/485 |
| 2007/0208198 A1 * | 9/2007 | Parker et al. | 562/485 |
| 2007/0208199 A1 * | 9/2007 | Parker et al. | 562/485 |
| 2007/0213557 A1 * | 9/2007 | Seiki et al. | 562/410 |
| 2008/0027243 A1 * | 1/2008 | Gibson et al. | 562/410 |
| 2008/0039648 A1 * | 2/2008 | Gibson et al. | 562/410 |
| 2008/0039649 A1 * | 2/2008 | Gibson et al. | 562/410 |
| 2008/0039650 A1 * | 2/2008 | Gibson et al. | 562/410 |
| 2008/0103333 A1 | 5/2008 | Nubel et al. | |

FOREIGN PATENT DOCUMENTS

| | | |
|---|---|---|
| EP | 0 181 127 A2 | 5/1986 |
| EP | 0 764 627 A1 | 3/1997 |
| EP | 0 579 715 B1 | 8/1997 |
| EP | 1 484 305 A1 | 8/2004 |
| EP | 1 484 306 A1 | 8/2004 |
| GB | 892766 A | 3/1962 |
| GB | 2067563 A | 7/1971 |
| GB | 1407705 | 9/1975 |
| JP | 46-14339 B | 11/1974 |
| JP | 51-145488 A | 12/1976 |
| JP | 49-123191 A | 2/1979 |
| JP | 54-25292 A | 2/1979 |
| JP | 62-25651 B2 | 6/1987 |
| JP | 09-048744 A | 2/1997 |
| JP | 9-157214 A | 6/1997 |
| JP | 10-114699 A | 5/1998 |
| JP | 11-349529 A | 12/1999 |
| JP | 3211396 B2 | 9/2001 |
| JP | 3232678 B2 | 11/2001 |
| JP | 59-53441 A | 3/2004 |
| KR | 1991-5989 B1 | 8/1991 |
| WO | WO 92/18453 | 10/1992 |
| WO | WO 92/18454 A1 | 10/1992 |
| WO | WO 93/24441 A | 12/1993 |
| WO | WO 97/27168 A1 | 7/1997 |
| WO | 9730963 * | 8/1997 |
| WO | WO 97/30963 A | 8/1997 |
| WO | WO 00/31014 A1 | 6/2000 |
| WO | WO 01/55075 A2 | 8/2001 |
| WO | 2004074231 A1 | 9/2004 |

OTHER PUBLICATIONS

BHS—Werk Sonthofen, *BHS-FEST Pressure Filter*, 1990, pamphlet, Santhofen, West Germany.

USPTO Office Action dated Oct. 20, 2004 for U.S. Appl. No. 10/455,017.

USPTO Office Action dated Jun. 6, 2005 for U.S. Appl. No. 10/455,017.

USPTO Office Action dated Nov. 10, 2005 for U.S. Appl. No. 10/455,017.

USPTO office action dated Jul. 19, 2006 for copending U.S. Appl. No. 10/455,017.

USPTO office action dated Jul. 19, 2006 for copending U.S. Appl. No. 10/455,018.

USPTO office action dated Dec. 27, 2006 for copending U.S. Appl. No. 10/455,018.

USPTO office action dated Jul. 19, 2006 for copending U.S. Appl. No. 10/455,016.

USPTO office action dated Jan. 18, 2007 for copending U.S. Appl. No. 10/455,017.

USPTO office action dated Nov. 30, 2006 for copending U.S. Appl. No. 10/975,256.

USPTO office action dated Nov. 30, 2006 for copending U.S. Appl. No. 10/975,252.

USPTO office action dated May 11, 2007 for copending U.S. Appl. No. 10/455,017.

USPTO office action dated May 14, 2007 for copending U.S. Appl. No. 10/455,018.

USPTO Office Action dated May 17, 2007 for copending U.S. Appl. No. 11/201,512.

USPTO Office Action dated Jul. 6, 2007 for copending U.S. Appl. No. 11/455,016.

Treybal, Robert E., "Stagewise Contact, Single-Stage Extraction," Mass-Transfer Operations, Third Edition, 1980, pp. 490-555, McGraw-Hill Book Company.

Copending U.S. Appl. No. 10/455,016, filed Jun. 5, 2003, Robert Lin.

Copending U.S. Appl. No. 10/455,017, filed Jun. 5, 2003, Robert Lin et al.

Copending U.S. Appl. No. 10/455,018, filed Jun. 5, 2003, Robert Lin et al.

Copending U.S. Appl. No. 10/874,419, filed Jun. 23, 2004, Kenny Randolph Parker et al.

Copending U.S. Appl. No. 10/948,591, filed Sep. 24, 2004, Robert Lin et al.

Copending U.S. Appl. No. 10/948,678, filed Sep., 24, 2004, Robert Lin et al.

Copending U.S. Appl. No. 10/975,256, filed Oct. 28, 2004, Philip Edward Gibson et al.

Copending U.S. Appl. No. 10/975,252, filed Oct. 28, 2004, Philip Edward Gibson et al.

Copending U.S. Appl. No. 11/181,214, filed Jul. 14, 2005, Robert Lin et al.

Copending U.S. Appl. No. 11/181,449, filed Jul. 14, 2005, Robert Lin et al.

Copending U.S. Appl. No. 11/201,512, filed Aug. 11, 2005, Robert Lin et al.

Copending U.S. Appl. No. 11/201,799, filed Aug. 11, 2005, Robert Lin et al.

Copending U.S. Appl. No. 11/655,395, filed Jan. 19, 2007, Philip E. Gibson et al.

Copending U.S. Appl. No. 11/655,317, filed Jan. 19, 2007, Philip E. Gibson et al.

Copending U.S. Appl. No. 11/655,396, filed Jan. 19, 2007, Kenny R. Parker et al.

Notice of Allowance dated Jul. 18, 2007 for copending U.S. Appl. No. 10/975,256.

Notice of Allowance dated Aug. 1, 2007 for copending U.S. Appl. No. 10/975,252.

Copending U.S. Appl. No. 11/842,413, filed Aug. 21, 2007, Kenny Randolph Parker et al.
USPTO Office Action dated Sep. 11, 2007 for copending U.S. Appl. No. 10/455,017.
USPTO Notice of Allowance dated Sep. 11, 2007 for copending U.S. Appl. No. 10/455,018.
USPTO Office Action dated Sep. 25, 2007 for copending U.S. Appl. No. 11/655,396.
USPTO Office Action dated Sep. 25, 2007 for copending U.S. Appl. No. 11/655,395.
USPTO Office Action dated Oct. 16, 2007 for copending U.S. Appl. No. 11/655,317.
USPTO Notice of Allowance dated Dec. 3, 2007 for copending U.S. Appl. No. 10/455,017.
USPTO Notice of Allowance dated Oct. 1, 2008 for copending U.S. Appl. No. 10/948,591.
USPTO Notice of Allowance dated Oct. 10, 2008 for copending U.S. Appl. No. 11/842,469.
USPTO Office Action dated Oct. 28, 2008 for copending U.S. Appl. No. 11/181,449.
USPTO Office Action dated Nov. 5, 2008 for copending U.S. Appl. No. 11/201,799.
USPTO Notice of Allowance dated Nov. 12, 2008 for copending U.S. Appl. No. 10/948,678.
USPTO Office Action dated Nov. 14, 2008 for copending U.S. Appl. No. 11/655,317.
USPTO Office Action dated Apr. 13, 2009 for copending U.S. Appl. No. 11/181,449.
USPTO Office Action dated Mar. 6, 2009 for copending U.S. Appl. No. 11/655,395.
USPTO Office Action dated Mar. 12, 2009 for copending U.S. Appl. No. 12/050,256.
USPTO Office Action dated Mar. 13, 2009 for copending U.S. Appl. No. 12/050,253.
USPTO Office Action dated May 21, 2009 for copending U.S. Appl. No. 11/181,214.
USPTO Notice of Allowance dated May 22, 2009 for copending U.S. Appl. No. 12/050,251.
USPTO Notice of Allowance dated Jun. 11, 2009 for copending U.S. Appl. No. 11/201,799.
USPTO Office Action dated Aug. 3, 2009 for copending U.S. Appl. No. 11/839,573.
USPTO Office Action dated Dec. 5, 2008 for copending U.S. Appl. No. 11/655,396.
USPTO Office Action dated Dec. 11, 2008 for copending U.S. Appl. No. 11/839,573.
USPTO Office Action dated Dec. 10, 2008 for copending U.S. Appl. No. 11/839,578.
USPTO Office Action dated Dec. 10, 2008 for copending U.S. Appl. No. 11/839,582.
USPTO Office Action dated Aug. 14, 2009 for copending U.S. Appl. No. 11/839,582.
USPTO Office Action dated Aug. 19, 2009 for copending U.S. Appl. No. 11/655,317.
USPTO Office Action dated Sep. 11, 2009 for copending U.S. Appl. No. 11/839,578.
USPTO Office Action dated Oct. 14, 2009 for copending U.S. Appl. No. 11/655,396.
USPTO Office Action dated Nov. 12, 2009 for copending U.S. Appl. No. 11/181,449.
USPTO Office Action dated Jan. 7, 2010 for copending U.S. Appl. No. 12/050,253.
USPTO Office Action dated Apr. 8, 2010 for copending U.S. Appl. No. 11/839,582.
USPTO Office Action dated Apr. 13, 2010 for copending U.S. Appl. No. 11/839,578.
USPTO Notice of Allowance dated May 5, 2010 for copending U.S. Appl. No. 11/839,582.
USPTO Office Action dated Jun. 8, 2010 for copending U.S. Appl. No. 11/655,396.
USPTO Office Action dated Jun. 18, 2010 for copending U.S. Appl. No. 11/181,449.
USPTO Office Action dated Jun. 18, 2010 for copending U.S. Appl. No. 12/050,256.
USPTO Office Action dated Dec. 2, 2009 for copending U.S. Appl. No. 11/655,395.
USPTO Office Action dated Dec. 2, 2009 for copending U.S. Appl. No. 11/839,573.
USPTO Office Action dated Dec. 11, 2009 for copending U.S. Appl. No. 12/050,256.
USPTO Office Action dated Sep. 10, 2010 for copending U.S. Appl. No. 12/050,258.
USPTO Office Action dated Sep. 23, 2010 for copending U.S. Appl. No. 11/839,578.
USPTO Notice of Allowance dated Nov. 23, 2010 for copending U.S. Appl. No. 11/544,396.
USPTO Office Action dated Jul. 9, 2010 for copending U.S. Appl. No. 11/839,573.
USPTO Office Action dated Jul. 20, 2010 for copending U.S. Appl. No. 11/655,395.
USPTO Office Action dated Feb. 14, 2008 for copending U.S. Appl. No. 11/842,469.
USPTO Office Action dated Mar. 7, 2008 for copending U.S. Appl. No. 10/948,591.
USPTO Office Action dated Mar. 5, 2008 for copending U.S. Appl. No. 11/655,317.
USPTO Office Action dated Mar. 4, 2008 for copending U.S. Appl. No. 11/839,578.
USPTO Office Action dated Mar. 5, 2008 for copending U.S. Appl. No. 11/655,396.
USPTO Office Action dated Mar. 14, 2008 for copending U.S. Appl. No. 10/948,678.
USPTO Office Action dated Mar. 11, 2008 for copending U.S. Appl. No. 11/655,395.
USPTO Office Action dated Mar. 11, 2008 for copending U.S. Appl. No. 11/839,582.
USPTO Office Action dated Mar. 11, 2008 for copending U.S. Appl. No. 11/839,573.
Copending U.S. Appl. No. 12/050,251, filed Mar. 18, 2008, Robert Lin et al.
Copending U.S. Appl. No. 12/050,253, filed Mar. 18, 2008, Robert Lin et al.
Copending U.S. Appl. No. 12/050,256, filed Mar. 18, 2008, Robert Lin et al.
Copending U.S. Appl. No. 12/050,258, filed Mar. 18, 2008, Robert Lin et al.
USPTO Office Action dated Apr. 4, 2008 for copending U.S. Appl. No. 11/181,449.
USPTO Office Action dated Apr. 25, 2008 for copending U.S. Appl. No. 11/181,214.
USPTO Notice of Allowance dated Dec. 6, 2010 for copending U.S. Appl. No. 11/181,449.
USPTO Notice of Allowance dated Dec. 16, 2010 for copending U.S. Appl. No. 11/655,395.

* cited by examiner

VERSATILE OXIDATION BYPRODUCT PURGE PROCESS

RELATED APPLICATIONS

This application is a divisional of application Ser. No. 11/655,395, entitled "VERSATILE OXIDATION BYPRODUCT PURGE PROCESS", filed Jan. 19, 2007 which claims the priority benefit of U.S. Provisional Pat. App. Ser. Nos. 60/777,829; 60/777,903; 60/777,905; 60/777,907; 60/777,992; 60/778,117; 60/778,120; 60/778,123; and 60/778,139, all filed Mar. 1, 2006. The foregoing applications are hereby incorporated by reference

BACKGROUND OF THE INVENTION

1. Field of the Invention

The present invention relates generally to a purge process for use in the production of a carboxylic acid. More specifically, the present invention relates to the use of a purge process for separating and routing various oxidation byproducts formed in a terephthalic acid production process.

2. Description of the Prior Art

In conventional terephthalic acid (TPA) production processes, para-xylene undergoes oxidation. In such processes, oxidation byproducts are produced along with the formation of TPA. Typically, such oxidation byproducts include the oxidation intermediates and side reaction products formed in the oxidation of para-xylene, as well as any impurities originating from the raw materials. Some of these byproducts are detrimental to the use of TPA in various production processes, such as for the production of polyethylene terephthalate (PET), dimethyl terephthalate (DMT), or cyclohexane dimethanol (CHDM). Accordingly, at least a portion of these detrimental oxidation byproducts are typically removed from the TPA production process in order to yield a commercially usable TPA product. On the other hand, some oxidation byproducts are not detrimental to these production processes. In fact, some oxidation byproducts, such as bi-functional compounds, are actually useful in a PET production process.

It is known in the art to employ a purge process to remove oxidation byproducts from TPA production processes, thus rendering the TPA product suitable for use in the various above-mentioned production processes. A purge process typically involves separating a portion of a mother liquor, generated from the separation of liquid from the product stream, to form a purge feed stream. The purge feed stream generally constitutes in the range of from 5 to 40 percent of the total mother liquor, but can be up to 100 percent of the mother liquor. In a typical conventional purge process, the purge feed stream contains acetic acid, catalyst, water, oxidation byproducts, and minor amounts of terephthalic acid. The purge feed stream in conventional processes is usually resolved into a catalyst rich stream and an oxidation byproduct rich stream. The catalyst rich stream is typically recycled to the oxidizer, whereas the oxidation byproduct rich stream is usually routed out of the TPA production process for waste treatment or destruction. In such a conventional process, the oxidation byproduct rich stream contains all of the different types of byproducts generated in the oxidation step. Thus, conventional purge processes expel both detrimental and non-detrimental oxidation byproducts from the TPA production process.

Accordingly, there is a need for a purge process that can differentiate detrimental oxidation byproducts from non-detrimental and/or beneficial oxidation byproducts. Such differentiation enables the operator to allow some or all of the non-detrimental and/or beneficial oxidation byproducts to exit the TPA production process along with the TPA product in order to increase product yield and decrease costs associated with waste treatment.

SUMMARY OF THE INVENTION

One embodiment of the present invention concerns a process for treating a purge feed stream comprising oxidation byproducts and one or more catalyst components, wherein the oxidation byproducts include benzoic acid (BA) and non-BA byproducts. The process of this embodiment comprises: (a) separating at least a portion of the purge feed stream into a non-BA byproduct rich stream and a catalyst and BA rich stream; and (b) separating at least a portion of the catalyst and BA rich stream into a catalyst rich stream and a BA rich stream.

Another embodiment of the present invention concerns a process for treating a purge feed stream comprising impurities and one or more catalyst components, wherein the impurities comprise mono-functional impurities and non-mono-functional impurities. The process of this embodiment comprises: (a) separating the purge feed stream into a mono-functional impurity depleted stream and a catalyst and mono-functional impurity rich mother liquor; and (b) separating the catalyst and mono-functional impurity rich mother liquor into a catalyst rich stream and a mono-functional impurity rich stream.

BRIEF DESCRIPTION OF THE DRAWING FIGURES

Figure 2:
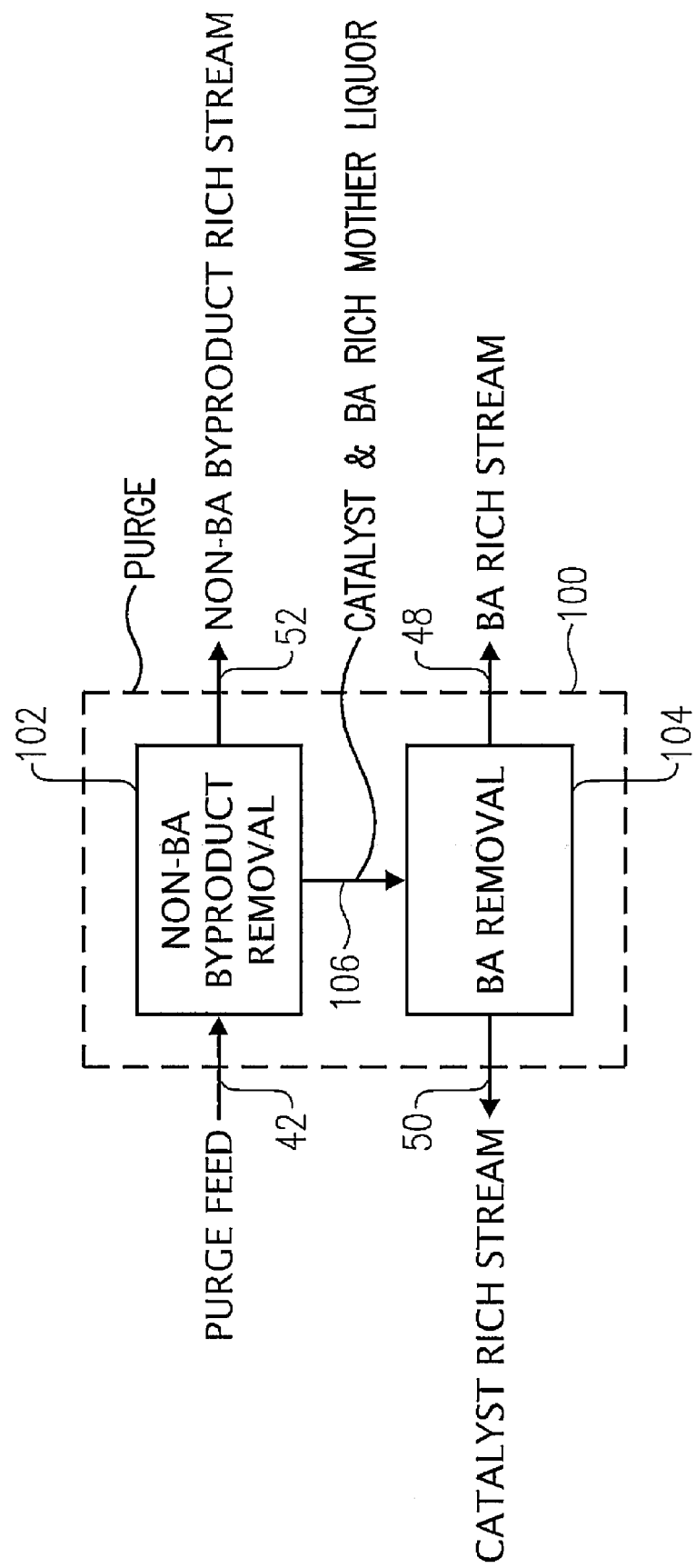
Figure 3:
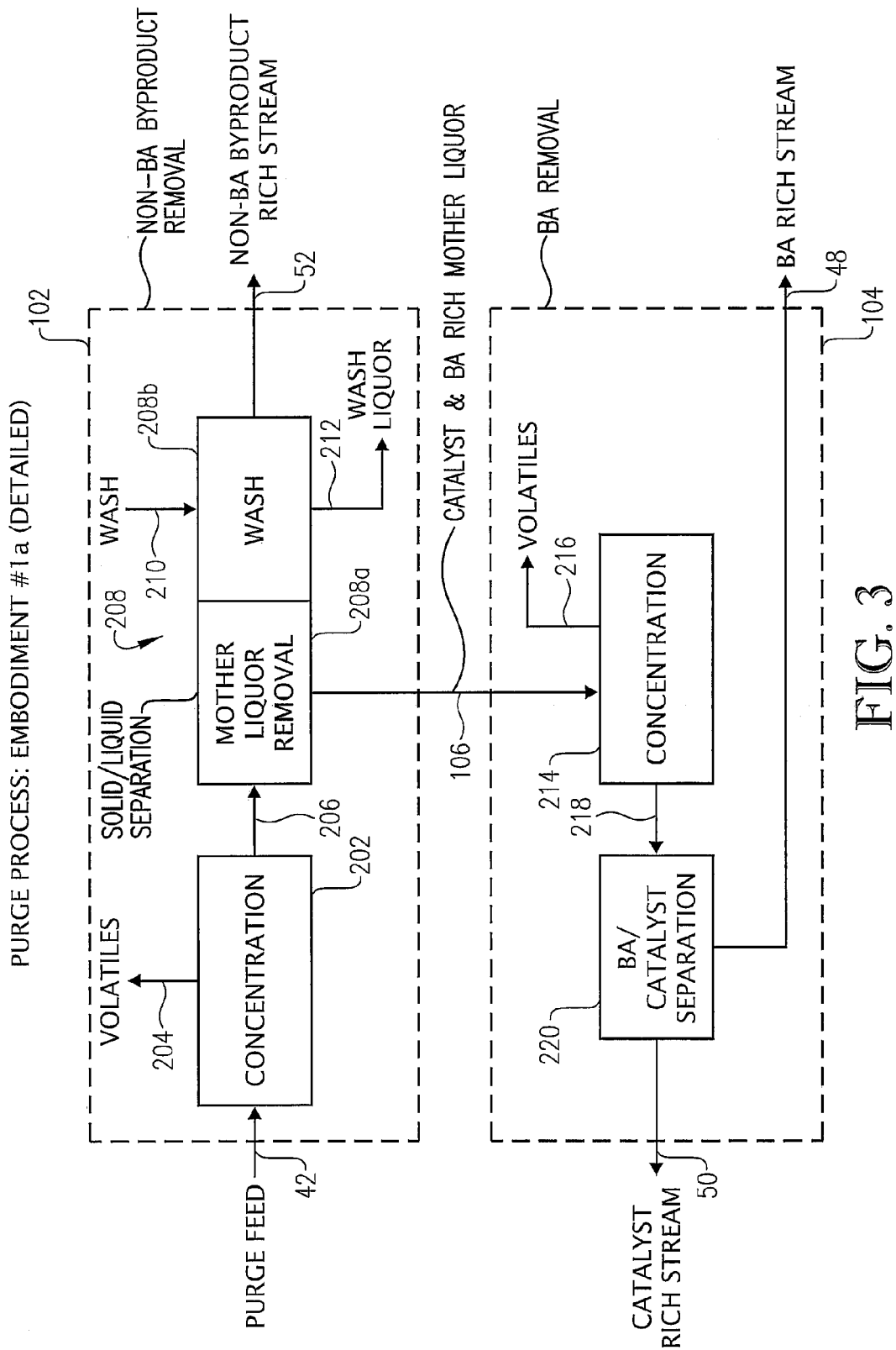
Figure 4:
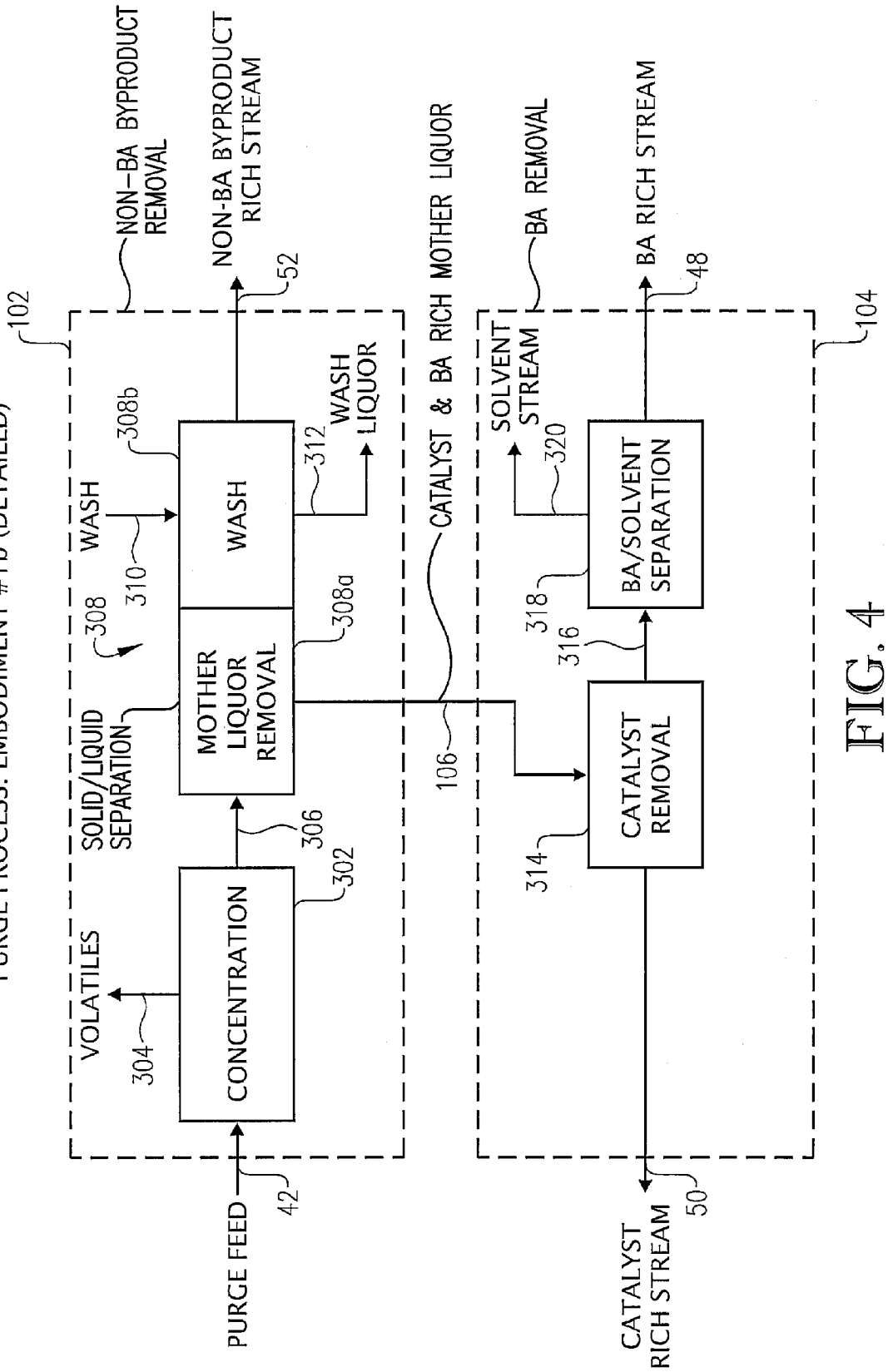
Figure 5:
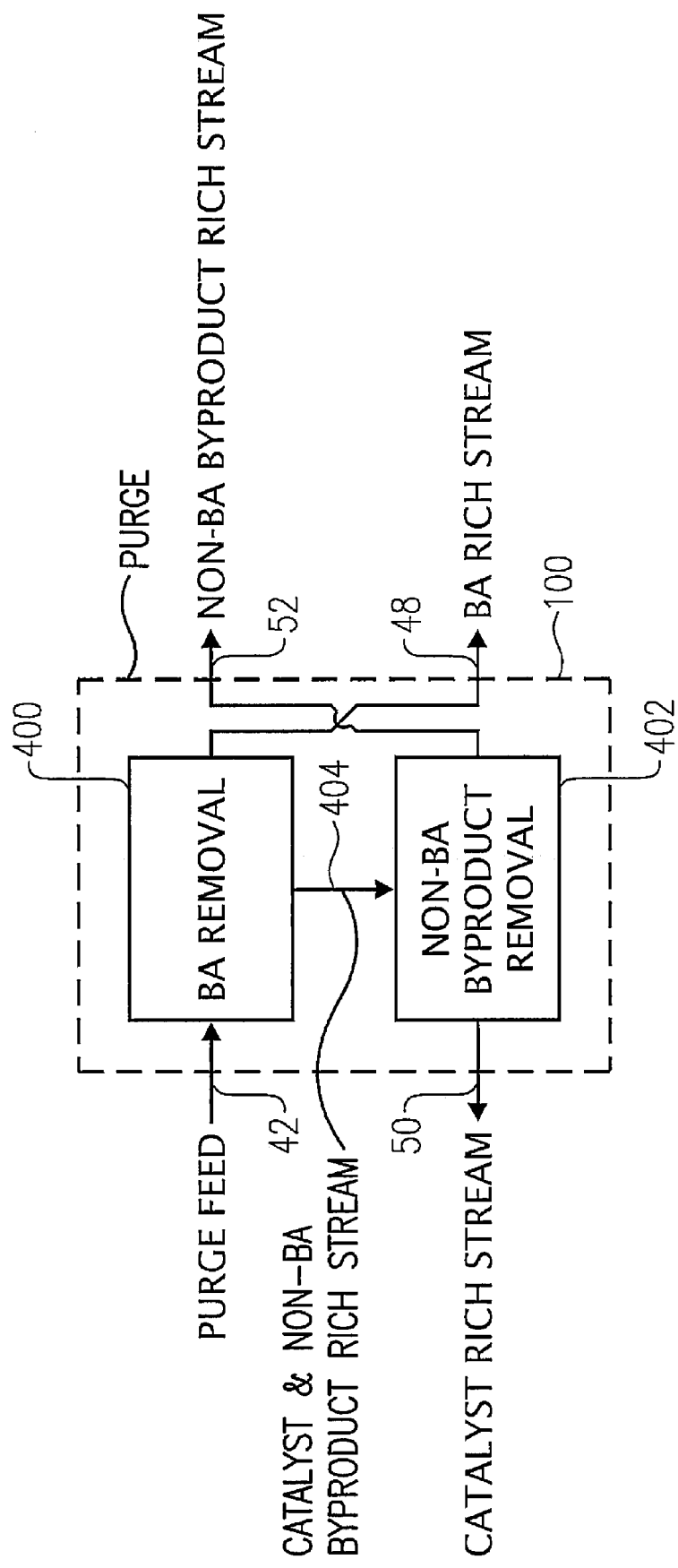
Figure 6:
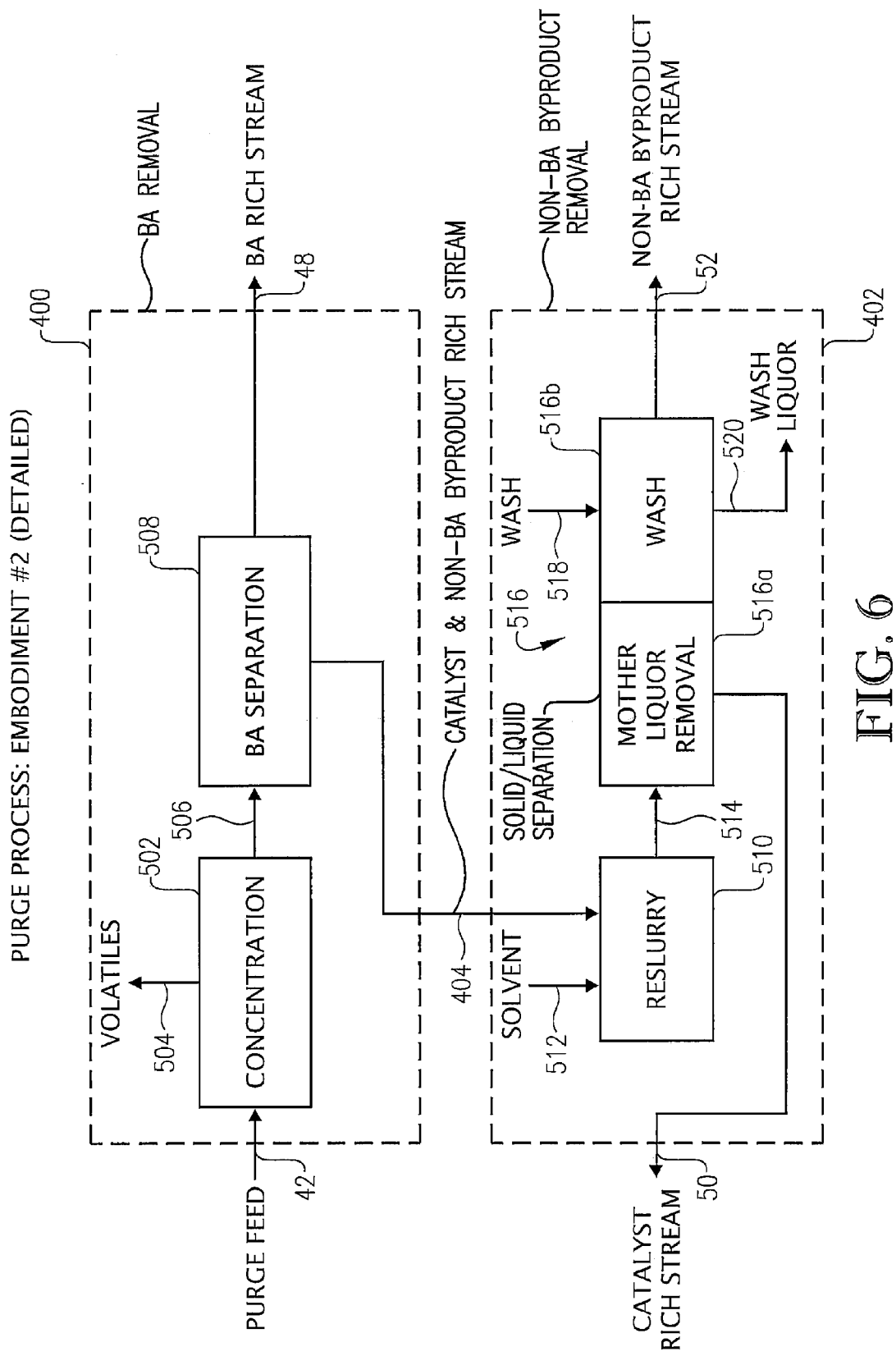

A preferred embodiment of the present invention is described in detail below with reference to the attached drawing figures, wherein:

FIG. 1 is a process flow diagram illustrating a system for the production and purification of carboxylic acid constructed in accordance with the present invention, particularly illustrating a configuration where the crude slurry from the oxidation reactor is subjected to purification, the resulting purified slurry is subjected to product isolation, and a portion of the mother liquor from the product isolation zone is employed as a feed to a purge treatment system;

FIG. 2 is a process flow diagram illustrating an overview of a purge treatment system constructed in accordance with a first embodiment of the present invention, particularly illustrating a configuration where the purge feed stream is subjected to non-benzoic acid (non-BA) byproduct removal and the resulting catalyst and benzoic acid (BA) rich mother liquor is subjected to BA removal;

FIG. 3 is a process flow diagram illustrating in detail a purge treatment system constructed in accordance with a first configuration of the first embodiment of the present invention, particularly illustrating a configuration where the purge feed stream is subjected to concentration, the resulting concentrated purge stream is subjected to solid/liquid separation, the resulting catalyst and BA rich mother liquor is subjected to concentration, and the resulting concentrated catalyst and BA rich mother liquor is subjected to BA/catalyst separation;

FIG. 4 is a process flow diagram illustrating in detail a purge treatment system constructed in accordance with a second configuration of the first embodiment of the present invention, particularly illustrating a configuration where the purge feed stream is subjected to concentration, the resulting concentrated purge stream is subjected to solid/liquid separation, the resulting catalyst and BA rich mother liquor is subjected to catalyst removal, and the resulting BA and solvent rich stream is subjected to BA/solvent separation;

FIG. 5 is a process flow diagram illustrating an overview of a purge treatment system constructed in accordance with a second embodiment of the present invention, particularly illustrating a configuration where the purge feed stream is subjected to BA removal and the resulting catalyst and non-BA byproduct rich stream is subjected to non-BA byproduct removal; and FIG. 6 is a process flow diagram illustrating in detail a purge treatment system constructed in accordance with the second embodiment of the present invention, particularly illustrating a configuration where the purge feed stream is subjected to concentration, the resulting concentrated purge stream is subjected to BA separation, the resulting catalyst and non-BA byproduct rich stream is reslurried, and the reslurried catalyst and non-BA byproduct rich stream is subjected to solid/liquid separation.

DETAILED DESCRIPTION

FIG. 1 illustrates an embodiment of the present invention where carboxylic acid produced in an oxidation reactor and purified in a purification reactor is subjected to product isolation/catalyst removal. A portion of the resulting mother liquor from the product isolation/catalyst removal zone is treated in a purge treatment zone and resolved into a catalyst rich stream, a benzoic acid (BA) rich stream, and a non-BA byproduct rich stream. Various embodiments of the purge zone are described in detail below with reference to FIGS. 2-6.

In the embodiment illustrated in FIG. 1, a predominately fluid-phase feed stream containing an oxidizable compound (e.g., para-xylene), a solvent (e.g., acetic acid and/or water), and a catalyst system (e.g., cobalt, manganese, and/or bromine) can be introduced into oxidation zone 10. A predominately gas-phase oxidant stream containing molecular oxygen can also be introduced into oxidation zone 10. The fluid- and gas-phase feed streams form a multi-phase reaction medium in oxidation zone 10. The oxidizable compound can undergo partial oxidation in a liquid phase of the reaction medium contained in oxidation zone 10.

In one embodiment of the present invention, oxidation zone 10 can comprise an agitated reactor. Agitation of the reaction medium in oxidation zone 10 can be provided by any means known in the art. As used herein, the term "agitation" shall denote work dissipated into the reaction medium causing fluid flow and/or mixing. In one embodiment, oxidation zone 10 can be a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In another embodiment of the present invention, oxidation zone 10 can comprise a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the terms "majority," "primarily," and "predominately" shall mean more than 50 percent.

The oxidizable compound present in the fluid-phase feed stream introduced into oxidation zone 10 can comprise at least one hydrocarbyl group. Also, the oxidizable compound can comprise an aromatic compound. In one embodiment, the oxidizable compound can comprise an aromatic compound with at least one attached hydrocarbyl group or at least one attached substituted hydrocarbyl group or at least one attached heteroatom or at least one attached carboxylic acid function (—COOH). In another embodiment, the oxidizable compound can comprise an aromatic compound with at least one attached hydrocarbyl group or at least one attached substituted hydrocarbyl group with each attached group comprising from 1 to 5 carbon atoms. In yet another embodiment, the oxidizable compound can be an aromatic compound having exactly two attached group with each attached group comprising exactly one carbon atom and consisting of methyl group and/or substituted methyl group and/or at most one carboxylic acid group. Suitable examples of the oxidizable compound include, but are not limited to, para-xylene, meta-xylene, para-tolualdehyde, meta-tolualdehyde, para-toluic acid, meta-toluic acid, and/or acetaldehyde. In one embodiment of the present invention, the oxidizable compound comprises para-xylene.

A "hydrocarbyl group," as defined herein, is at least one carbon atom that is bonded only to hydrogen atoms and/or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. "Aromatic compounds," as defined herein, comprise an aromatic ring and can comprise at least 6 carbon atoms and can also comprise only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the fluid-phase feed stream introduced into oxidation zone 10 can be in the range of from about 4 to about 20 weight percent, or in the range of from 6 to 15 weight percent.

The solvent present in the fluid-phase feed stream introduced into primary oxidation reactor 10 can comprise an acid component and a water component. The solvent can be present in the fluid-phase feed stream at a concentration in the range of from about 60 to about 98 weight percent, in the range of from about 80 to about 96 weight percent, or in the range of from 85 to 94 weight percent. The acid component of the solvent can be an organic low molecular weight monocarboxylic acid having from 1 to 6 carbon atoms, or 2 carbon atoms. In one embodiment, the acid component of the solvent can comprise acetic acid. The acid component can make up at least about 75 weight percent of the solvent, at least about 80 weight percent of the solvent, or in the range of from 85 to 98 weight percent of the solvent, with the balance being water.

As mentioned above, the fluid-phase feed stream introduced into oxidation zone 10 can also include a catalyst system. The catalyst system can be a homogeneous, liquid-phase catalyst system capable of promoting at least partial oxidation of the oxidizable compound. Also, the catalyst system can comprise at least one multivalent transition metal. In one embodiment, the catalyst system can comprise cobalt, bromine, and/or manganese.

When cobalt is present in the catalyst system, the fluid-phase feed stream can comprise cobalt in an amount such that the concentration of cobalt in the liquid phase of the reaction medium is maintained in the range of from about 300 to about 6,000 parts per million by weight (ppmw), in the range of from about 700 to about 4,200 ppmw, or in the range of from 1,200 to 3,000 ppmw. When bromine is present in the catalyst system, the fluid-phase feed stream can comprise bromine in an amount such that the concentration of bromine in the liquid phase of the reaction medium is maintained in the range of from about 300 to about 5,000 ppmw, in the range of from about 600 to about 4,000 ppmw, or in the range of from 900 to 3,000 ppmw. When manganese is present in the catalyst system, the liquid-phase feed stream can comprise manganese in an amount such that the concentration of manganese in the liquid phase of the reaction medium is maintained in the range of from about 20 to about 1,000 ppmw, in the range of from about 40 to about 500 ppmw, or in the range of from 50 to 200 ppmw.

In one embodiment of the present invention, cobalt and bromine can both be present in the catalyst system. The weight ratio of cobalt to bromine (Co:Br) in the catalyst system can be in the range of from about 0.25:1 to about 4:1, in the range of from about 0.5:1 to about 3:1, or in the range of from 0.75:1 to 2:1. In another embodiment, cobalt and manganese can both be present in the catalyst system. The weight ratio of cobalt to manganese (Co:Mn) in the catalyst system can be in the range of from about 0.3:1 to about 40:1, in the range of from about 5:1 to about 30:1, or in the range of from 10:1 to 25:1.

During oxidation, the oxidizable compound (e.g., para-xylene) can be continuously introduced into oxidation zone 10 at a rate of at least about 5,000 kilograms per hour, at a rate in the range of from about 10,000 to about 80,000 kilograms per hour, or in the range of from 20,000 to 50,000 kilograms per hour. During oxidation, the ratio of the mass flow rate of the solvent to the mass flow rate of the oxidizable compound entering oxidation zone 10 can be maintained in the range of from about 2:1 to about 50:1, in the range of from about 5:1 to about 40:1, or in the range of from 7.5:1 to 25:1.

The predominately gas-phase oxidant stream introduced into oxidation zone 10 can comprise in the range of from about 5 to about 40 mole percent molecular oxygen, in the range of from about 15 to about 30 mole percent molecular oxygen, or in the range of from 18 to 24 mole percent molecular oxygen. The balance of the oxidant stream can be comprised primarily of a gas or gases, such as nitrogen, that are inert to oxidation. In one embodiment, the oxidant stream consists essentially of molecular oxygen and nitrogen. In another embodiment, the oxidant stream can be dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in oxidation zone 10, the oxidant stream can be introduced into oxidation zone 10 in an amount that provides molecular oxygen somewhat exceeding the stoichiometric oxygen demand. Thus, the ratio of the mass flow rate of the oxidant stream (e.g., air) to the mass flow rate of the oxidizable compound (e.g., para-xylene) entering oxidation zone 10 can be maintained in the range of from about 0.5:1 to about 20:1, in the range of from about 1:1 to about 10:1, or in the range of from 2:1 to 6:1.

The liquid-phase oxidation reaction carried out in oxidation zone 10 can be a precipitating reaction that generates solids. In one embodiment, the liquid-phase oxidation carried out in oxidation zone 10 can cause at least about 10 weight percent of the oxidizable compound (e.g., para-xylene) introduced into oxidation zone 10 to form solids (e.g., crude terephthalic acid (CTA) particles) in the reaction medium. In another embodiment, the liquid-phase oxidation carried out in oxidation zone 10 can cause at least about 50 weight percent of the oxidizable compound (e.g., para-xylene) introduced into oxidation zone 10 to form solids (e.g., CTA particles) in the reaction medium. In yet another embodiment, the liquid-phase oxidation carried out in oxidation zone 10 can cause at least about 90 weight percent of the oxidizable compound (e.g., para-xylene) introduced into oxidation zone 10 to form solids (e.g., CTA particles) in the reaction medium. In one embodiment, the solids content of the reaction medium can be maintained in the range of from about 5 to about 40 weight percent, in the range of from about 10 to about 35 weight percent, or in the range of from 15 to 30 weight percent. As used herein, the term "solids content" shall denote the weight percent solids in a multi-phase mixture.

During oxidation in oxidation zone 10, the multi-phase reaction medium can be maintained at an elevated temperature in the range of from about 125 to about 200° C., in the range of from about 150 to about 180° C., or in the range of from 155 to 165° C. The overhead pressure in oxidation zone 10 can be maintained in the range of from about 1 to about 20 bar gauge (barg), in the range of from about 2 to about 12 barg, or in the range of from 4 to 8 barg.

In the embodiment of FIG. 1, a crude slurry can be withdrawn from an outlet of oxidation zone 10 via line 12. The solid phase of the crude slurry in line 12 can be formed primarily of solid particles of CTA. The liquid phase of the crude slurry in line 12 can be a liquid mother liquor comprising at least a portion of the solvent, one or more catalyst components, and minor amounts of dissolved terephthalic acid (TPA). The solids content of the crude slurry in line 12 can be the same as the solids content of the reaction medium in oxidation zone 10, discussed above.

In one embodiment of the present invention, the crude slurry in line 12 can comprise impurities. As used herein, the term "impurities" is defined as any substance other than TPA, solvent, catalyst, and water. Such impurities can include oxidation byproducts formed during the at least partial oxidation of the above-mentioned oxidizable compound (e.g., para-xylene) including, but not limited to, benzoic acid (BA), bromo-benzoic acid, bromo-acetic acid, isophthalic acid, trimellitic acid, 2,5,4'-tricarboxybiphenyl, 2,5,4'-tricarboxybenzophenone, para-toluic acid (p-TAc), 4-carboxybenzaldehyde (4-CBA), monocarboxyfluorenones, monocarboxyfluorenes, and/or dicarboxyfluorenones.

In one embodiment of the present invention, the impurities in the crude slurry in line 12 can be classified according to their functionality in a polyester polymerization process, such as, for example, in the production of polyethylene terephthalate (PET). Some impurities can be mono-functional while others can be non-mono-functional in a process for producing a polyester (e.g., PET). As used herein, an impurity that is "mono-functional" is defined as having only one reactive moiety in a process for producing a polyester (e.g., PET). Typically, such reactive moieties can include carboxyl and/or hydroxyl group. Mono-functional impurities include, but are not limited to, BA, bromo-benzoic acid, bromo-acetic acid, 4-CBA, p-TAc, monocarboxyfluorenones, and/or monocarboxyfluorenes. Non-mono-functional impurities can comprise any impurity having less than or greater than one reactive moiety in a process for producing a polyester (e.g., PET). Non-mono-functional impurities include, but are not limited to, isophthalic acid, trimellitic acid, 2,5,4'-tricarboxybiphenyl, 2,5,4'-tricarboxybenzophenone, and dicarboxyfluorenones.

Subsequent to removal from oxidation zone 10, the crude slurry can optionally be introduced into purification zone 14 via line 12. In one embodiment, the crude slurry can be treated in purification zone 14 such that the concentration of at least one of the above-mentioned impurities in the crude slurry is reduced, thereby producing a purified slurry. Such reduction in the concentration of impurities in the TPA can be accomplished by oxidative digestion, hydrogenation, and/or dissolution/recrystallization.

In one embodiment of the present invention, the crude slurry fed to purification zone 14 can have a 4-CBA content of at least about 100 parts per million based on the weight of the solids in the crude slurry ($ppmw_{cs}$), in the range of from about 200 to about 10,000 $ppmw_{cs}$, or in the range of from 800 to 5,000 $ppmw_{cs}$. The crude slurry fed to purification zone 14 can have a p-TAc content of at least about 250 $ppmw_{cs}$, in the range of from about 300 to about 5,000 $ppmw_{cs}$, or in the range of from 400 to 1,500 $ppmw_{cs}$. The purified slurry exiting purification zone 14 can have a 4-CBA content of less than about 150 parts per million based on the weight of the solids in the purified slurry ($ppmw_{ps}$), less than about 100 $ppmw_{ps}$, or less than 50 $ppmw_{ps}$. The purified slurry exiting purification zone 14 can have a p-TAc content of less than about 300 $ppmw_{ps}$, less than about 200 $ppmw_{ps}$, or less than 150 $ppmw_p$. In one embodiment, treatment of the crude slurry in purification zone 14 can cause the purified slurry exiting purification zone 14 to have a 4-CBA and/or p-TAc content that is at least about 50 percent less than the 4-CBA and/or p-TAc content of the crude slurry fed to purification zone 14, at least about 85 percent less, or at least 95 percent less. By way of illustration, if the 4-CBA content of the crude slurry fed to purification zone 14 is 200 $ppmw_{cs}$ and the 4-CBA content of the purified slurry exiting purification zone 14 is 100 $ppmw_{ps}$, then the 4-CBA content of the purified slurry is 50 percent less than the 4-CBA content of the crude slurry.

In one embodiment of the present invention, the crude slurry can be subjected to purification by oxidative digestion in purification zone 14. As used herein, the term "oxidative digestion" denotes a process step or step where a feed comprising solid particles is subjected to oxidation under conditions sufficient to permit oxidation of at least a portion of the impurities originally trapped in the solid particles. Purification zone 14 can comprise one or more reactors or zones. In one embodiment, purification zone 14 can comprise one or more mechanically-agitated reactors. A secondary oxidant stream, which can have the same composition as the gas-phase oxidant stream fed to oxidation zone 10, can be introduced into purification zone 14 to provide the molecular oxygen required for oxidative digestion. Additional oxidation catalyst can be added if necessary. In an alternative embodiment of the present invention, a stream comprising hydrogen can be introduced into purification zone 14 for at least partial hydrogenation of the crude slurry.

When oxidative digestion is employed in purification zone 14, the temperature at which oxidative digestion is carried out can be at least about 10° C. greater than the temperature of oxidation in oxidation zone 10, in the range of from about 20 to about 80° C. greater, or in the range of from 30 to 50° C. greater. The additional heat required for the operation of purification zone 14 can be provided by supplying a vaporized solvent to purification zone 14 and allowing the vaporized solvent to condense therein. The oxidative digestion temperature in purification zone 14 can be maintained in the range of from about 180 to about 240° C., in the range of from about 190 to about 220° C., or in the range of from 200 to 210° C. The oxidative digestion pressure in purification zone 14 can be maintained in the range of from about 100 to about 350 pounds per square inch gauge (pig), in the range of from about 175 to about 275 pig, or in the range of from 185 to 225 pig.

In one embodiment of the present invention, purification zone 14 can include two digestion reactors/zones—an initial digester and a final digester. When purification zone 14 includes an initial digester and a final digester, the final digester can be operated at a lower temperature and pressure than the initial digester. In one embodiment, the operating temperature of the final digester can be at least about 2° C. lower than the operating temperature of the initial digester, or in the range of from about 5 to about 15° C. lower than the operating temperature of the initial digester. In one embodiment, the operating pressure of the final digester can be at least about 5 pig lower than the operating pressure of the initial digester, or in the range of from about 10 to about 50 pig lower than the operating pressure of the initial digester. The operating temperature of the initial digester can be in the range of from about 195 to about 225° C., in the range of from 205 to 215° C., or about 210° C. The operating pressure of the initial digester can be in the range of from about 215 to about 235 pig, or about 225 pig. The operating temperature of the final digester can be in the range of from about 190 to about 220° C., in the range of from 200 to 210° C., or about 205° C. The operating pressure of the final digester can be in the range of from about 190 to 210 pig, or about 200 pig.

In one embodiment of the present invention, purification zone 14 can comprise optional first and second solvent swap zones. Optional first and second solvent swap zones can operate to replace at least a portion of the existing solvent in a slurry with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with optional counter current washing. The replacement oxidation solvent can have substantially the same composition as the solvent introduced into oxidation zone 10, as described above.

In one embodiment, the crude slurry fed to purification zone 14 can be treated in the optional first solvent swap zone prior to purification of the crude slurry by the above-mentioned oxidative digestion. In another embodiment, a purified slurry resulting from oxidative digestion of the crude slurry can be treated in the optional second solvent swap zone.

Optionally, at least a portion of the displaced oxidation solvent from the optional first and/or second solvent swap zones can be discharged from purification zone 14 via line 38. At least a portion of the displaced oxidation solvent in line 38 can be routed to solids removal zone 32 via line 40, purge treatment zone 100 via line 38a, and/or oxidation zone 10 via line 38b.

In another embodiment of the present invention, purification zone 14 can comprise an optional crystallization zone and/or an optional cooling zone. A purified slurry resulting from the above-mentioned oxidative digestion of the crude slurry can be treated in the optional crystallization zone to at least partially increase the particle size distribution of the purified slurry. Optional crystallization zone can comprise any equipment known in the art that can operate to increase the particle size distribution of the purified slurry. When an optional cooling zone is employed, the purified slurry can be cooled therein to a temperature in the range of from about 20 to about 195° C. When both a crystallization zone and a cooling zone are employed, the purified slurry can be treated first in the crystallization zone and subsequently in the cooling zone.

Referring again to FIG. 1, a purified slurry can be withdrawn from an outlet of purification zone 14 via line 16. The solid phase of the purified slurry can be formed primarily of purified terephthalic acid (PTA) particles, while the liquid phase can be formed of a mother liquor. The solids content of the purified slurry in line 16 can be in the range of from about 1 to about 50 percent by weight, in the range of from about 5 to about 40 weight percent, or in the range of from 20 to 35 weight percent. The purified slurry in line 16 can be introduced into product isolation/catalyst removal zone 18 for at least partial recovery of the solid PTA particles.

Optionally, at least a portion of the crude slurry in line 12 can be introduced into product isolation/catalyst removal zone 18 via line 12a. As mentioned above, the solid phase of the crude slurry can be formed primarily of CTA particles, while the liquid phase can be formed of a mother liquor. The solids content of the crude slurry in line 12a can be in the range of from about 1 to about 50 percent by weight, in the range of from about 5 to about 40 weight percent by weight, or in the range of from 20 to 35 percent by weight. The crude slurry in line 12a can be introduced into product isolation/catalyst removal zone 18 for recovery of the solid CTA particles.

Product isolation/catalyst removal zone 18 can separate the crude slurry and/or the purified slurry into a predominately fluid phase mother liquor and a wet cake. Product isolation/catalyst removal zone 18 can comprise any method of solid/liquid separation known in the art that is capable of generating a wet cake and a mother liquor stream. In addition, it may be desirable for product isolation/catalyst removal zone 18 to have the capability of washing the wet cake. Suitable equipment for use in product isolation/catalyst removal zone 18 includes, but is not limited to, a pressure drum filter, a vacuum drum filter, a vacuum belt filter, multiple solid bowl centrifuges with optional counter current wash, or a perforated centrifuge.

In one embodiment of the present invention, a wash stream can be introduced into product isolation/catalyst removal zone 18 to wash at least a portion of the wet cake generated in product isolation/catalyst removal zone 18, thereby producing a washed wet cake. In one embodiment, the wash stream can comprise acetic acid and/or water. Optionally, after washing the wet cake, the used wash liquor can be withdrawn from product isolation/catalyst removal zone 18, and at least a portion of the wash liquor can be routed, either directly or indirectly, to oxidation zone 10.

The above-mentioned wet cake generated in product isolation/catalyst removal zone 18 can be discharged via line 20. In one embodiment of the present invention, the wet cake generated in product isolation/catalyst removal zone 18 can primarily comprise solid particles of TPA. The solid TPA particles can comprise CTA and/or PTA particles. The wet cake can comprise in the range of from about 5 to about 30 weight percent liquid, in the range of from about 10 to about 25 weight percent liquid, or in the range of from 12 to 23 weight percent liquid. Additionally, the TPA product wet cake in line 20 can comprise oxidation byproducts, as discussed above. In one embodiment, the TPA product in line 20 can comprise a cumulative concentration of mono-functional oxidation byproducts of less than about 1,000 ppmw, less than about 750 ppmw, or less than 500 ppmw.

In one embodiment of the present invention, the wet cake in line 20 can be introduced into drying zone 22 via line 20 to thereby produce a dry TPA particulate product comprising solid TPA particles. Drying zone 22 can comprise any drying device known in the art that can produce a dried TPA particulate product comprising less than about 5 weight percent liquid, less than about 3 weight percent liquid, or less than 1 weight percent liquid. Dried TPA particulate product can be discharged from drying zone 22 via line 24.

In another embodiment, the wet cake in line 20 can be introduced into solvent swap zone 26 to produce a wet TPA particulate product comprising solid TPA particles. Solvent swap zone 26 can operate to replace at least a portion of the liquid in the wet cake with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with counter current washing. Wet TPA particulate product can be discharged from solvent swap zone 26 via line 28. The wet TPA particulate product can comprise in the range of from about 5 to about 30 weight percent liquid, in the range of from about 10 to about 25 weight percent liquid, or in the range of from 12 to 23 weight percent liquid.

Referring still to FIG. 1, the above-mentioned mother liquor can be discharged from product isolation/catalyst removal zone 18 via line 30. In one embodiment of the present invention, at least a portion of the mother liquor can optionally be introduced into solids removal zone 32. Solids removal zone 32 can comprise any equipment known in the art that is operable to remove a sufficient amount of solids from the mother liquor to produce a solids-depleted mother liquor comprising less than about 5 weight percent solids, less than about 2 weight percent solids, or less than 1 weight percent solids. Suitable equipment that may be employed in solids removal zone 32 includes a pressure filter, such as, for example, a filter press, a candle filter, a pressure leaf filter, and/or a cartridge filter. In one embodiment, solids removal zone 32 can be operated at a temperature in the range of from about 20 to about 195° C. and a pressure in the range of from about 750 to about 3750 torr during solids removal. The solids-depleted mother liquor can be discharged from solids removal zone 32 via line 34. In one embodiment of the present invention, at least a portion of the solids removed from the mother liquor in solids removal zone 32 can be discharged via line 36 and can be routed to product isolation/catalyst removal zone 18 via line 36a and/or to line 20 via line 36b.

As mentioned above, at least a portion of the displaced oxidation solvent from purification zone 14 can also optionally be treated in solids removal zone 32. Such displaced oxidation solvent can be withdrawn from purification zone 14 via line 38 and introduced into solids removal zone 32 via line 40. When displaced oxidation solvent from oxidation zone 14 is treated in solids removal zone 32, the resulting solids-depleted displaced oxidation solvent can be combined with the solids-depleted mother liquor and can be discharged via line 34.

In one embodiment of the present invention, at least a portion of the optionally solids-depleted mother liquor in line 34 can be withdrawn from line 34 via line 42 to form a purge feed stream. The amount of mother liquor withdrawn by line 42 to form the purge feed stream can be in the range of from about 1 to about 55 percent of the total weight of the mother liquor, in the range of from about 5 to about 45 percent by weight, or in the range of from 10 to 35 percent by weight. Optionally, at least a portion of the displaced oxidation solvent discharged from purification zone 14 in line 38 can be combined with the purge feed stream via line 38a. In another embodiment, at least a portion of the remaining mother liquor in line 34 can be routed, either directly or indirectly, to oxidation zone 10 via line 44. Optionally, at least a portion of the wash liquor discharged from product isolation/catalyst removal zone 18 can be combined with at least a portion of the mother liquor in line 44 prior to introduction into oxidation zone 10.

In one embodiment of the present invention, the mother liquor in line 34, and consequently the purge feed stream in line 42, can comprise solvent, one or more catalyst components, oxidation byproducts, and TPA. The solvent in the mother liquor in line 34 and the purge feed stream in line 42 can comprise a monocarboxylic acid. In one embodiment, the solvent can comprise water and/or acetic acid. The mother liquor in line 34 and the purge feed stream in line 42 can comprise solvent in an amount of at least about 85 weight percent, at least about 95 weight percent, or at least 99 weight percent.

The catalyst components in the mother liquor in line 34 and the purge feed stream in line 42 can comprise the catalyst components as described above with reference to the catalyst system introduced into oxidation zone 10. In one embodiment, the catalyst components can comprise cobalt, manganese, and/or bromine. The mother liquor in line 34 and the purge feed stream in line 42 can have a cumulative concentration of all of the catalyst components in the range of from about 500 to about 20,000 ppmw, in the range of from about 1,000 to about 15,000 ppmw, or in the range of from 1,500 to 10,000 ppmw.

The oxidation byproducts in the mother liquor in line 34 and the purge feed stream in line 42 can comprise one or more of the oxidation byproducts discussed above. In one embodiment, the oxidation byproducts in the mother liquor in line 34 and the purge feed stream in line 42 can comprise both BA and non-BA byproducts. As used herein, the term "non-BA byproducts" is defined as any oxidation byproduct that is not benzoic acid. Non-BA byproducts include, but are not limited to, isophthalic acid (IPA), phthalic acid (PA), trimellitic acid, 2,5,4'-tricarboxybiphenyl, 2,5,4'-tricarboxybenzophenone, p-TAc, 4-CBA, naphthalene dicarboxylic acid, monocarboxyfluorenones, monocarboxyfluorenes, and/or dicarboxyfluorenones. In one embodiment, the mother liquor in line 34 and the purge feed stream in line 42 can comprise BA in an amount in the range of from about 500 to about 150,000 ppmw based on the weight of the purge feed stream, in the range of from about 1,000 to about 100,000 ppmw, or in the range of from 2,000 to 50,000 ppmw. Additionally, the mother liquor in line 34 and the purge feed stream in line 42 can have a cumulative concentration of non-BA byproducts in the range of from about 500 to about 50,000 ppmw, in the range of from about 1,000 to about 20,000 ppmw, or in the range of from 2,000 to 10,000 ppmw.

In one embodiment of the present invention, the mother liquor in line 34 and the purge feed stream in line 42 can comprise solids in an amount of less than about 5 weight percent, less than about 2 weight percent, or less than 1 weight percent. Additionally, the purge feed stream can have a temperature of less than about 240° C., in the range of from about 20 to about 200° C., or in the range of from 50 to 100° C.

Referring still to FIG. 1, the purge feed stream can be introduced into a purge treatment zone 100 via line 42. As will be discussed in greater detail below, the purge treatment zone 100 can separate the purge feed stream into a catalyst rich stream, a BA rich stream (i.e., a mono-functional impurity rich stream), and a non-BA byproduct rich stream (i.e., a mono-functional impurity depleted stream). The BA rich stream can be discharged from purge treatment zone 100 via line 48, the catalyst rich stream can be discharged from purge treatment zone 100 via line 50, and the non-BA byproduct rich stream can be discharged from purge treatment zone 100 via line 52.

The BA rich stream in line 48 can have a relatively higher concentration of BA on a weight basis compared to the BA concentration of the purge feed stream in line 42. In one embodiment of the present invention, the BA rich stream in line 48 can have a concentration of BA that is at least about 1.5 times the concentration of BA in the purge feed stream on a weight basis, at least about 5 times the concentration of BA in the purge feed stream on a weight basis, or at least 10 times the concentration of BA in the purge feed stream on a weight basis. In one embodiment, BA can be the primary oxidation byproduct in the BA rich stream. Depending of the temperature and pressure of the BA rich stream upon exiting purge treatment zone 100, the BA rich stream in line 48 can predominately comprise solids or fluid. Thus, in one embodiment, the BA rich stream in line 48 can comprise at least about 50 weight percent fluid, at least about 70 weight percent fluid, or at least 90 weight percent fluid. In an alternate embodiment, the BA rich stream in line 48 can comprise at least about 50 weight percent solids, at least about 70 weight percent solids, or at least 90 weight percent solids.

The catalyst rich stream in line 50 can have a relatively higher cumulative concentration of all of the catalyst components on a weight basis compared to the cumulative concentration of all of the catalyst components in the purge feed stream in line 42. In one embodiment of the present invention, the catalyst rich stream in line 50 can have a cumulative concentration of all of the catalyst components that is at least about 1.5 times the cumulative concentration of all of the catalyst components in the purge feed stream on a weight basis, at least about 5 times the cumulative concentration of all of the catalyst components in the purge feed stream on a weight basis, or at least 10 times the cumulative concentration of all of the catalyst components in the purge feed stream on a weight basis. Depending of the temperature and pressure of the catalyst rich stream upon exiting purge treatment zone 100, the catalyst rich stream in line 50 can predominately comprise solids or fluid. Thus, in one embodiment, the catalyst rich stream in line 50 can comprise at least about 50 weight percent fluid, at least about 70 weight percent fluid, or at least 90 weight percent fluid. In an alternate embodiment, the catalyst rich stream in line 50 can comprise at least about 50 weight percent solids, at least about 70 weight percent solids, or at least 90 weight percent solids.

The non-BA byproduct rich stream in line 52 can have a relatively higher cumulative concentration of non-BA byproducts on a weight basis compared to the cumulative concentration of non-BA byproducts in the purge feed stream in line 42. In one embodiment of the present invention, the non-BA byproduct rich stream in line 52 can have a cumulative concentration of non-BA byproducts that is at least about 1.5 times the cumulative concentration of non-BA byproducts in the purge feed stream on a weight basis, at least about 5 times the cumulative concentration of non-BA byproducts in the purge feed stream on a weight basis, or at least 10 times the cumulative concentration of non-BA byproducts in the purge feed stream on a weight basis. In one embodiment, non-BA byproducts can cumulatively be the primary oxidation byproducts in the non-BA byproduct rich stream. The non-BA byproduct rich stream in line 52 can be in the form of a wet cake, comprising in the range of from about 5 to about 30 weight percent liquid, in the range of from 10 to about 25 weight percent liquid, or in the range of from 12 to 23 weight percent liquid.

In one embodiment of the present invention, at least a portion of the BA rich stream, the catalyst rich stream, and the non-BA byproduct rich stream can be routed to different locations. Such locations include, but are not limited to, various points in a TPA production process, an IPA production process, a phthalic acid (PA) production process, a BA production process, a naphthalene-dicarboxylic acid (NDA) production process, a dimethylterephthalate (DMT) production process, a dimethylnaphthalate (DMN) production process, a cyclohexane dimethanol (CHDM) production process, a dimethylcyclohexanedicarboxylate (DMCD) production process, a cyclohexanedicarboxylic acid (CHDA) production process, a polyethylene terephthalate (PET) production process, a production process for any isomers of NDA, DMT, DMN, CHDM, DMCD, CHDA, a copolyester production process, a polymer production process employing one or more of TPA, IPA, PA, BA, NDA, DMT, DMN, CHDM, DMCD, CHDA, or any isomers thereof as one component and/or as a monomer, and/or outside the TPA, IPA, PA, BA, NDA, DMT, DMN, CHDM, DMCD, CHDA, PET, or polymer production processes.

In one embodiment, the amount of BA that exits the TPA production process with the TPA product and/or is combined with the TPA product downstream of the TPA production process can be sufficient to result in a TPA product comprising BA in an amount of less than about 1000 ppmw, less than about 500 ppmw, or less than 250 ppmw. In another embodiment, the rate at which BA exits the TPA production process with the TPA product and/or is combined with the TPA product downstream of the TPA production process can be less than about 50 percent, less than about 10 percent, less than about 1 percent, or less than 0.1 percent of the make-rate of BA in the TPA production process. As used herein with reference to BA, when no purification step (e.g., purification zone 14) is employed in the TPA production process, the term "make-rate" is defined as the difference between the mass per unit time of BA entering the oxidation step (e.g., oxidation zone 10) and the mass per unit time of BA exiting the oxidation step. When a purification step is employed in the TPA production process, the term "make-rate" when referring to BA is defined as the difference between the mass per unit time of BA entering the oxidation step (e.g., oxidation zone 10) and the mass per unit time of BA exiting the purification step (e.g., purification zone 14). By way of illustration, for a TPA production process that employs a purification step, if BA enters the oxidation step of the TPA production process at a rate of 50 kilograms per hour (kg/hr), and BA exits the purification step at a rate of 150 kg/hr, then the make-rate of BA in the TPA production process is 100 kg/hr.

In another embodiment, at least a portion of the BA rich stream can exit the process depicted in FIG. 1 and be routed to a purification and recovery process, a subsequent chemical process, and/or a waste treatment or disposal process. Such waste treatment or disposal processes include, but are not limited to, sale, burial, incineration, neutralization, anaerobic and/or aerobic digestion, treatment in a waste oxidizer, and/or treatment in a waste reactor. In one embodiment of the present invention, at least a portion of the BA rich stream can be routed to a waste treatment process where at least about 50 weight percent, at least about 60 weight percent, or at least 70 weight percent of the BA present in the BA rich stream is treated.

As mentioned above, the catalyst rich stream in line 50 can be routed to various points in a TPA production process. In one embodiment of the present invention, at least a portion of the catalyst rich stream in line 50 can be routed, either directly or indirectly, to oxidation zone 10, where at least about 50 weight percent, at least about 60 weight percent, or at least 70 weight percent of the catalyst components of the catalyst rich stream are introduced into oxidization zone 10. In one embodiment, prior to routing, a liquid can optionally be added to the catalyst rich stream in line 50 to produce a reslurried catalyst rich stream. The reslurried catalyst rich stream can comprise at least about 35 weight percent liquid, at least about 50 weight percent liquid, or at least 65 weight percent liquid. The liquid added to the catalyst rich stream can be, for example, acetic acid and/or water.

Referring still to FIG. 1, as noted above, the non-BA byproduct rich stream in line 52 can be routed to various points in the depicted TPA production process. Such routing includes, but is not limited to, returning at least a portion of the non-BA byproduct rich stream, either directly or indirectly, to oxidation zone 10 and/or purification zone 14. In one embodiment, at least a portion of the non-BA byproduct rich stream can be routed such that at least a portion of the non-BA byproducts in said non-BA byproduct rich stream exit the TPA production process with the dry TPA product discharged from line 24 and/or with the wet TPA product discharged from line 28. For example, at least a portion of the non-BA byproduct rich stream can be introduced into the purified slurry in line 16 and/or into the product slurry/cake in line 20 and allowed to exit the TPA production process with the TPA product. In another embodiment, at least a portion of the non-BA byproducts in the non-BA byproduct rich stream can be combined with the TPA product downstream of the TPA production process. In one embodiment, at least about 5 weight percent, at least about 25 weight percent, at least about 50 weight percent, or at least 75 weight percent of the non-BA byproducts in the non-BA byproduct rich stream can be allowed to exit the TPA production process with the TPA product and/or can be combined with the TPA product downstream of the TPA production process.

In one embodiment, the cumulative rate at which the non-BA byproducts exit the TPA production process with the TPA product and/or are combined with the TPA product downstream of the TPA production process can be at least about 5 percent, at least about 10 percent, at least about 20 percent, or at least 50 percent of the make-rate of the non-BA byproducts in the TPA production process. As used herein with reference to non-BA byproducts, when no purification step (e.g., purification zone 14) is employed in the TPA production process, the term "make-rate" is defined as the difference between the mass per unit time of non-BA byproducts entering the oxidation step (e.g., oxidation zone 10) and the mass per unit time of non-BA byproducts exiting the oxidation step. When a purification step is employed in the TPA production process, the term "make-rate" when referring to non-BA byproducts is defined as the difference between the mass per unit time of non-BA byproducts entering the oxidation step (e.g., oxidation zone 10) and the mass per unit time of non-BA byproducts exiting the purification step (e.g., purification zone 14). By way of illustration, for a TPA production process that employs a purification step, if non-BA byproducts enter the oxidation step of the TPA production process at a rate of 50 kg/hr, and non-BA byproducts exit the purification step at a rate of 150 kg/hr, then the make-rate of non-BA byproducts in the TPA production process is 100 kg/hr.

In another embodiment, the non-BA byproduct rich stream can exit the process depicted in FIG. 1 and can be routed to a purification and recovery process, a process utilizing non-BA byproducts for making non-BA byproduct derivatives, and/or a waste treatment or disposal process. Such waste treatment or disposal processes include, but are not limited to, sale, burial, incineration, neutralization, anaerobic and/or aerobic digestion, treatment in a waste oxidizer, and/or treatment in a waste reactor.

As mentioned above, the non-BA byproduct rich stream in line 52 can be in the form of a wet cake. In one embodiment of the present invention, prior to routing the non-BA byproduct rich stream, at least a portion the non-BA byproduct rich stream may optionally be dried in drying zone 54. Drying zone 54 can comprise any drying device known in the art that can produce a dried non-BA byproduct rich stream comprising less than about 5 weight percent liquid, less than about 3 weight percent liquid, or less than 1 weight percent liquid. The optionally dried non-BA byproduct rich stream can be discharged from drying zone 54 via line 56.

In another embodiment, prior to routing the non-BA byproduct rich stream, a liquid may be added to at least a portion of the non-BA byproduct rich stream in reslurry zone 58 to produce a reslurried non-BA byproduct rich stream. The reslurried non-BA byproduct rich stream can be discharged from reslurry zone 58 via line 60. The reslurried non-BA byproduct rich stream can comprise at least about 35 weight percent liquid, at least about 50 weight percent liquid, or at least 65 weight percent liquid. The liquid added to the non-BA byproduct rich stream in reslurry zone 58 can comprise acetic acid and/or water.

FIG. 2 illustrates an overview of one embodiment of purge treatment zone 100, briefly discussed above with reference to FIG. 1. In the embodiment of FIG. 2, purge treatment zone 100 comprises a non-BA byproduct removal zone 102 and a BA removal zone 104. The purge feed stream in line 42 can initially be introduced into non-BA byproduct removal zone 102. As will be discussed in greater detail below, non-BA byproduct removal zone 102 can separate the purge feed stream into the above-mentioned non-BA byproduct rich stream and a catalyst and BA rich mother liquor (i.e., a catalyst and mono-functional impurity rich mother liquor). The non-BA byproduct rich stream can be discharged from non-BA byproduct removal zone 102 via line 52, and the catalyst and BA rich mother liquor can be discharged via line 106.

In one embodiment of the present invention, the catalyst and BA rich mother liquor in line 106 can comprise one or more catalyst components, BA, and solvent. The catalyst and BA rich mother liquor can comprise solids in an amount of less than about 5 weight percent, less than about 3 weight percent, or less than 1 weight percent. The solvent in the catalyst and BA rich mother liquor can comprise acetic acid and/or water. The catalyst components in the catalyst and BA rich mother liquor can comprise cobalt, manganese, and/or bromine, as discussed above in relation to the catalyst system introduced into oxidation zone 10 of FIG. 1.

The catalyst and BA rich mother liquor in line 106 can have a relatively higher concentration of BA and catalyst components on a weight basis compared to the concentration of BA and catalyst components in the purge feed stream in line 42. In one embodiment, the catalyst and BA rich mother liquor in line 106 can have a cumulative concentration of all of the catalyst components that is at least about 1.5 times the cumulative concentration of all of the catalyst components in the purge feed stream on a weight basis, at least about 5 times the cumulative concentration of all of the catalyst components in the purge feed stream on a weight basis, or at least 10 times the cumulative concentration of all of the catalyst components in the purge feed stream on a weight basis. Furthermore, the catalyst and BA rich mother liquor in line 106 can have a concentration of BA that is at least about 1.5 times the concentration of BA in the purge feed stream on a weight basis, at least about 5 times the concentration of BA in the purge feed stream on a weight basis, or at least 10 times the concentration of BA in the purge feed stream on a weight basis.

In the embodiment of FIG. 2, the catalyst and BA rich mother liquor can be introduced into BA removal zone 104 via line 106. As will be discussed in greater detail below, BA removal zone 104 can separate the catalyst and BA rich mother liquor into the above-mentioned BA rich stream and the above-mentioned catalyst rich stream. The BA rich stream can be discharged from BA removal zone 104 via line 48 and the catalyst rich stream can be discharged via line 50.

FIG. 3 illustrates in detail one configuration of non-BA byproduct removal zone 102 and BA removal zone 104. In the embodiment of FIG. 3, non-BA byproduct removal zone 102 comprises concentration section 202 and solid/liquid separation section 208. In this embodiment, the purge feed stream can initially be introduced into concentration section 202 via line 42. Concentration section 202 can operate to remove at least a portion of the volatile compounds contained in the purge feed stream. In one embodiment, the volatile compounds comprise at least a portion of the solvent in the purge feed stream. The solvent can comprise water and/or acetic acid. Concentration section 202 can remove at least about 30, at least about 45, or at least 60 weight percent of the volatile compounds in the purge feed stream. Volatile compounds can be discharged from concentration section 202 via line 204. In one embodiment of the present invention, at least a portion of the volatiles in line 204 can be routed, either directly or indirectly, to oxidation zone 10 depicted in FIG. 1.

Any equipment known in the industry capable of removing at least a portion of the volatile compounds from the purge feed stream may be employed in concentration section 202. Examples of suitable equipment include, but are not limited to, one or more evaporators. In one embodiment, concentration section 202 can comprise at least two evaporators. When two evaporators are employed, each one individually can be operated under vacuum at reduced temperature, or can be operated at elevated temperature and pressure. In one embodiment, each evaporator can be operated at a temperature in the range of from about 40 to about 180° C. and a pressure in the range of from about 50 to about 4500 torr during concentration. Suitable equipment for use in concentration section 202 includes, but is not limited to, a simple agitated tank, a flash evaporator, an advancing front crystallizer, a thin film evaporator, a scraped thin film evaporator, and/or a falling film evaporator.

In the embodiment of FIG. 3, a concentrated purge feed stream can be discharged from concentration section 202 via line 206. The solids content of the concentrated purge feed stream in line 206 can be at least about 1.5 times, at least about 5 times, or at least 10 times the solids content of the unconcentrated purge feed stream in line 42, where solids content is measured on a weight basis. The concentrated purge feed stream can comprise solids in an amount in the range of from about 5 to about 70 weight percent, or in the range of from 10 to 40 weight percent. Also, the concentrated purge feed stream can comprise one or more catalyst components, BA and non-BA oxidation byproducts, TPA particles, and solvent, each as discussed above.

The concentrated purge feed stream can be introduced into solid/liquid separation section 208 via line 206. Solid/liquid separation section 208 can separate the concentrated purge feed stream into a predominately fluid phase catalyst and BA rich mother liquor and a wet cake. In the embodiment of FIG. 3, solid/liquid separation section 208 comprises mother liquor removal section 208*a* and wash section 208*b*. Mother liquor removal section 208*a* can operate to separate the concentrated purge feed stream into the above-mentioned catalyst and BA rich mother liquor and an initial wet cake. The catalyst and BA rich mother liquor can be discharged from mother liquor removal section 208*a* via line 106. The initial wet cake can be introduced into wash section 208*b*. At least a portion of the initial wet cake can then be washed with the wash feed introduced into wash section 208*b* via line 210 to produce a washed wet cake. The wash feed in line 210 can comprise water and/or acetic acid. Furthermore, the wash feed can have a temperature in the range of from about the freezing point of the wash feed to about the boiling point of the wash feed, in the range of from about 20 to about 110° C., or in the range of from 40 to 90° C. The wash feed can operate to remove at least a portion of catalyst components from the wet cake. After washing the wet cake, the resulting wash liquor can be discharged from wash section 208b via line 212, and the washed wet cake can be discharged via line 52. In one embodiment, the above-mentioned non-BA byproduct rich stream comprises at least a portion of the washed wet cake.

Solid/liquid separation section 208 can comprise any solid/liquid separation device known in the art. Suitable equipment for use in solid/liquid separation section 208 includes, but is not limited to, a pressure drum filter, a vacuum drum filter, a vacuum belt filter, multiple solid bowl centrifuges with counter current wash, or a perforated centrifuge. In one embodiment, solid/liquid separation section 208 can be operated at a temperature in the range of from about 20 to about 170° C. and a pressure in the range of from about 375 to about 4500 torr during separation.

As mentioned above, the wash liquor can be discharged from solid/liquid separation section 208 via line 212. In one embodiment, at least a portion of the wash liquor in line 212 can be routed, either directly or indirectly, to oxidation zone 10 as depicted in FIG. 1. Optionally, at least a portion of the wash liquor in line 212 can be concentrated prior to introduction in oxidation zone 10. The optional concentrator can be any device known in the art capable of concentrating the wash liquor stream, such as, for example, membrane separation or evaporation. In another embodiment, at least a portion of the wash liquor in line 212 can be routed to a waste treatment facility.

Referring still to FIG. 3, BA removal zone 104 comprises concentration section 214 and BA/catalyst separation section 220. In one embodiment, the catalyst and BA rich mother liquor in line 106 can initially be introduced into concentration section 214. Concentration section 214 can operate to remove at least a portion of the volatile compounds contained in the catalyst and BA rich mother liquor. In one embodiment, the volatile compounds comprise at least a portion of the solvent in the catalyst and BA rich mother liquor. The solvent can comprise water and/or acetic acid. Concentration section 214 can remove at least about 50, at least about 70, or at least 90 weight percent of the solvent in the catalyst and BA rich mother liquor. Evaporated compounds can be discharged from concentration section 214 via line 216.

Any equipment known in the industry capable of removing at least a portion of the volatile compounds from the catalyst and BA rich mother liquor can be employed in concentration section 214. Examples of suitable equipment include, but are not limited to, a simple agitated tank, a flash evaporator, an advancing front crystallizer, a thin film evaporator, a scraped thin film evaporator, or a falling film evaporator. In one embodiment, concentration section 214 can be operated at a pressure in the range of from about 50 to about 800 torr during concentration. Additionally, concentration section 214 can be operated at a temperature of at least about 120° C., or at least 130° C. during concentration.

In the embodiment of FIG. 3, a concentrated catalyst and BA rich mother liquor (i.e., a mono-functional impurity rich slurry) can be discharged from concentration section 214 via line 218. The concentrated catalyst and BA rich mother liquor can comprise one or more catalyst components, BA, and solvent. The concentration of all the catalyst components and BA of the concentrated catalyst and BA rich mother liquor can be at least about 1.5 times, at least about 5 times, or at least 10 times the concentration of all the catalyst components and BA of the unconcentrated catalyst and BA rich mother liquor in line 106.

The concentrated catalyst and BA rich mother liquor can be introduced into BA/catalyst separation section (i.e., mono-functional impurity removal section) 220 via line 218. BA/catalyst separation section 220 operates to separate the concentrated catalyst and BA rich mother liquor into the above-mentioned catalyst rich stream and the above-mentioned BA rich stream. In one embodiment, separation of the concentrated catalyst and BA rich mother liquor can be accomplished by evaporating and removing at least a portion of the BA in the concentrated catalyst and BA rich mother liquor. Any dryer known in the art that can evaporate and remove at least about 50 weight percent, at least about 70 weight percent, or at least 90 weight percent of the BA in the concentrated catalyst and BA rich mother liquor can be used. A suitable example of a commercially available dryer that can be employed in BA/catalyst separation section 220 includes, but is not limited to, a LIST dryer. In one embodiment, BA/catalyst separation section 220 can be operated at a temperature in the range of from about 170 to about 250° C. and a pressure in the range of from about 50 to about 760 torr during separation. The catalyst rich stream can be discharged from BA/catalyst separation section 220 via line 50, and the BA rich stream can be discharged via line 48.

FIG. 4 illustrates in detail a second configuration of non-BA byproduct removal zone 102 and BA removal zone 104. Non-BA byproduct removal zone 102 comprises concentration section 302 and solid/liquid separation section 308. In the embodiment of FIG. 4, concentration section 302 and solid/liquid separation section 308 are operated in substantially the same manner as discussed above with reference to concentration section 202 and solid/liquid separation section 208 of FIG. 3. Additionally, the composition and treatment of the volatiles in line 304, the concentrated purge feed stream in line 306, the wash feed in line 310, and the wash liquor in line 312 are substantially the same as discussed above with reference to the volatiles in line 204, the concentrated purge feed stream in line 206, the wash feed in line 210, and the wash liquor in line 212 of FIG. 3. The above-mentioned non-BA byproduct rich stream can be discharged from solid/liquid separation section 308 via line 52, and the above-mentioned catalyst and BA rich mother liquor can be discharged via line 106.

In the embodiment of FIG. 4, BA removal zone 104 comprises catalyst removal section 314 and BA/solvent separation section 318. In one embodiment, the catalyst and BA rich mother liquor in line 106 can initially be introduced into catalyst removal section 314. Catalyst removal section 314 can operate to remove at least a portion of the BA and solvent in the catalyst and BA rich mother liquor, generating the above-mentioned catalyst rich stream and a BA and solvent rich stream (i.e., a mono-functional impurity and solvent rich stream). Removal of BA and solvent in catalyst removal section 314 can be accomplished by evaporating and removing at least a portion of the BA and solvent from the catalyst and BA rich mother liquor. In one embodiment, at least about 50 weight percent, at least about 70 weight percent, or at least 90 weight percent of the BA and solvent in the catalyst and BA rich mother liquor can be removed in catalyst removal section 314. Any dryer known in the art that can evaporate and remove at least a portion of the BA and solvent in the catalyst and BA rich mother liquor can be used. A suitable example of a commercially available dryer that can be employed in catalyst removal section 314 includes, but is not limited to, a LIST dryer. In one embodiment, catalyst removal 314 can be operated at a temperature in the range of from about 170 to about 250° C. and a pressure in the range of from about 50 to about 760 torr during catalyst removal.

As mentioned above, catalyst removal zone 314 generates the catalyst rich stream and a BA and solvent rich stream. The catalyst rich stream can be discharged from catalyst removal zone 314 via line 50. The BA and solvent rich stream can be discharged from catalyst removal section 314 via line 316. In one embodiment, the BA and solvent rich stream can be a predominately fluid phase stream and can comprise at least two portions having different volatilities (i.e., a lower volatility portion and a higher volatility portion). The lower volatility portion can comprise BA and the higher volatility portion can comprise solvent. The solvent can comprise acetic acid and/or water.

In the embodiment of FIG. 4, the BA and solvent rich stream can be introduced into BA/solvent separation section (i.e., mono-functional impurity/solvent separation section) 318 via line 316. BA/solvent separation section 318 can separate the BA and solvent rich stream into the above-mentioned BA rich stream and a solvent rich stream. The separation of the BA and solvent rich stream can be accomplished by fluid/fluid separation. Any fluid/fluid separation device known in the art capable of separating two fluid phases may be used in BA/solvent separation section 318. Such devices include, but are not limited to, a dryer, an evaporator, a partial condenser, and/or distillation devices. In one embodiment, BA/solvent separation section 318 can be operated at a temperature in the range of from about 170 to about 250° C. and a pressure in the range of from about 50 to about 760 torr during separation.

The BA rich stream can be discharged from BA/solvent separation section 318 via line 48. The solvent rich stream can be discharged from BA/solvent separation section 314 via line 320. In one embodiment, the solvent rich stream can comprise a higher concentration of solvent than the BA and solvent rich stream in line 316. The solvent rich stream can have a concentration of solvent that is at least about 1.5 times the concentration of solvent in the BA and solvent rich stream on a weight basis, at least about 5 times the concentration of solvent in the solvent and BA rich stream on a weight basis, or at least 10 times the concentration of solvent in the solvent and BA rich stream on a weight basis. In one embodiment, at least a portion of the solvent rich stream in line 320 can be routed, either directly or indirectly, to oxidation zone 10 depicted in FIG. 1.

FIG. 5 illustrates an overview of another embodiment of purge treatment zone 100, briefly discussed above with reference to FIG. 1. In the embodiment of FIG. 5, purge treatment zone 100 comprises BA removal zone 400 and non-BA byproduct removal zone 402. The purge feed stream in line 42 can initially be introduced into BA removal zone 400. As will be discussed in greater detail below, BA removal zone 400 can separate the purge feed stream into the above-mentioned BA rich stream and a catalyst and non-BA byproduct rich stream (i.e., a catalyst and non-mono-functional impurity rich stream). The BA rich stream can be discharged from BA removal zone 400 via line 48, and the catalyst and non-BA byproduct rich stream can be discharged via line 404.

In one embodiment of the present invention, the catalyst and non-BA byproduct rich stream can comprise one or more catalyst components, non-BA byproducts, and solvent. Depending of the temperature and pressure of the catalyst and non-BA byproduct rich stream upon exiting BA removal zone 400, the catalyst and non-BA byproduct rich stream in line 404 can predominately comprise solids or fluid. Thus, in one embodiment, the catalyst and non-BA byproduct rich stream in line 404 can comprise at least about 50 weight percent fluid, at least about 70 weight percent fluid, or at least 90 weight percent fluid. In an alternate embodiment, the catalyst and non-BA byproduct rich stream in line 404 can comprise at least about 50 weight percent solids, at least about 70 weight percent solids, or at least 90 weight percent solids. The solvent in the catalyst and non-BA byproduct rich stream can comprise acetic acid and/or water. The catalyst components in the catalyst and non-BA byproduct rich stream can comprise cobalt, manganese, and/or bromine, as discussed above in relation to the catalyst system introduced into oxidation zone 10 of FIG. 1.

The catalyst and non-BA byproduct rich stream in line 404 can have a relatively higher concentration of catalyst components and non-BA byproducts on a weight basis compared to the concentration of catalyst components and non-BA byproducts in the purge feed stream in line 42. In one embodiment, the catalyst and non-BA byproduct rich stream in line 404 can have a cumulative concentration of all of the catalyst components that is at least about 1.5 times the cumulative concentration of all of the catalyst components in the purge feed stream on a weight basis, at least about 5 times the cumulative concentration of all of the catalyst components in the purge feed stream on a weight basis, or at least 10 times the cumulative concentration of all of the catalyst components in the purge feed stream on a weight basis. Furthermore, the catalyst and non-BA byproduct rich stream in line 404 can have a cumulative concentration of non-BA byproducts that is at least about 1.5 times the cumulative concentration of non-BA byproducts in the purge feed stream on a weight basis, at least about 5 times the cumulative concentration of non-BA byproducts in the purge feed stream on a weight basis, or at least 10 times the cumulative concentration of non-BA byproducts in the purge feed stream on a weight basis.

In the embodiment of FIG. 5, the catalyst and non-BA byproduct rich stream can be introduced into non-BA byproduct removal zone 402 via line 404. As will be discussed in greater detail below, non-BA byproduct removal zone 402 can separate the catalyst and non-BA byproduct rich stream into the above-mentioned non-BA byproduct rich stream and the above-mentioned catalyst rich stream. The non-BA byproduct rich stream can be discharged from non-BA byproduct removal zone 402 via line 52 and the catalyst rich stream can be discharged via line 50.

FIG. 6 illustrates in detail one configuration of BA removal zone 400 and non-BA byproduct removal zone 402. In the embodiment of FIG. 6, BA removal zone 400 comprises concentration section 502 and BA separation section 508. In this embodiment, the purge feed stream in line 42 can initially be introduced into concentration section 502. Concentration section 502 can operate to remove at least a portion of the volatile compounds contained in the purge feed stream. Concentration section 502 is operated in substantially the same manner as discussed above with reference to concentration section 202 of FIG. 3. Volatiles can be discharged from concentration section 502 via line 504. The composition and treatment of the volatiles in line 504 is substantially the same as discussed above with reference to the volatiles in line 204 of FIG. 3. A concentrated purge feed stream can be discharged from concentration section 502 via line 506. The composition of the concentrated purge feed stream in line 506 is substantially the same as discussed above with reference to the concentrated purge feed stream in line 206 of FIG. 3.

Referring still to FIG. 6, the concentrated purge feed stream in line 506 can be introduced into BA separation section (i.e., mono-functional impurity removal section) 508. BA separation section 508 can operate to separate the concentrated purge feed stream into the above-mentioned BA rich stream and the above-mentioned catalyst and non-BA byproduct rich stream. In one embodiment, BA separation can be achieved by evaporating and removing at least a portion of the BA from the concentrated purge feed stream. The evaporation can be achieved by heating the concentrated purge feed stream in BA separation section 508 to at least about 123° C. at atmospheric pressure. In another embodiment, BA separation section 508 can be operated at a pressure in the range of from about 50 to about 760 torr during evaporation. Additionally, BA separation section 508 can be operated at a temperature in the range of from about 123 to about 250° C. during evaporation. At least about 40 weight percent, at least about 70 weight percent, or at least 90 weight percent of the BA contained in the concentrated purge feed stream can be removed in BA separation section 508. Equipment suitable for use in BA separation section 508 includes, but is not limited to, a LIST dryer, a pot distillation device, a partial condenser, or a thin film evaporator. The BA rich stream can be discharged from BA separation section 508 via line 48, and the catalyst and non-BA byproduct rich stream can be discharged via line 404.

In the embodiment of FIG. 6, non-BA byproduct removal zone 402 comprises reslurry section 510 and solid/liquid separation section 516. In one embodiment, the catalyst and non-BA byproduct rich stream in line 404 can initially be introduced into reslurry section 510. Reslurry section 510 can be operated to add a liquid to the catalyst and non-BA byproduct rich stream, thereby generating a reslurried catalyst and non-BA byproduct rich stream. The liquid added to the catalyst and non-BA byproduct rich stream in reslurry section 510 can be introduced into reslurry section 510 via line 512. In one embodiment, the liquid in line 512 can be a solvent, which can comprise acetic acid and/or water. Equipment suitable for use in reslurry section 510 can include any equipment known in the art that can accomplish mixing a liquid stream and a solid stream to generate a slurry. Optionally, reslurry section 510 can comprise a step of crystallization in order to increase particle size distribution.

The reslurried catalyst and non-BA byproduct rich stream can be discharged from reslurry section 510 via line 514. In one embodiment, the reslurried catalyst and non-BA byproduct rich stream can comprise one or more catalyst components, non-BA byproducts, and/or solvent. The solvent can comprise acetic acid and/or water. The catalyst components can comprise cobalt, manganese, and/or bromine, as discussed above in relation to the catalyst system introduced into oxidation zone 10 of FIG. 1. The reslurried catalyst and non-BA byproduct rich stream can comprise solids in an amount in the range of from about 0 to about 65 weight percent, or in the range of from 10 to 40 weight percent.

The reslurried catalyst and non-BA byproduct rich stream can be introduced into solid/liquid separation section 516 via line 514. Solid/liquid separation section 514 can separate the reslurried catalyst and non-BA byproduct rich stream into a predominately fluid phase mother liquor (e.g., the above-mentioned catalyst rich stream) and a wet cake. In the embodiment of FIG. 6, solid/liquid separation section 516 comprises mother liquor removal section 516a and wash section 516b. Mother liquor removal section 516a can operate to separate the reslurried catalyst and non-BA byproduct rich stream into the above-mentioned catalyst rich stream and an initial wet cake. The catalyst rich stream can be discharged from mother liquor removal section 516a via line 50. The initial wet cake can be introduced into wash section 516b. At least a portion of the initial wet cake can then be washed with the wash feed introduced into wash section 516b via line 518 to produce a washed wet cake. The wash feed in line 518 can comprise water and/or acetic acid. The wash feed can operate to remove at least a portion of catalyst components from the wet cake. After washing the wet cake, the resulting wash liquor can be discharged from wash section 516b via line 520, and the washed wet cake can be discharged via line 52. In one embodiment, the above-mentioned non-BA byproduct rich stream can comprise at least a portion of the washed wet cake.

Solid/liquid separation section 516 can comprise any solid/liquid separation device known in the art. Suitable equipment that can be used in solid/liquid separation section 516 includes, but is not limited to, a pressure drum filter, a vacuum drum filter, a vacuum belt filter, multiple solid bowl centrifuges with counter current wash, or a perforated centrifuge. In one embodiment, solid/liquid separation section 516 can be operated at a temperature in the range of from about 20 to about 170° C. and a pressure in the range of from about 375 to about 4500 torr during separation.

As mentioned above, the wash liquor can be discharged from solid/liquid separation section 516 via line 520. In one embodiment, at least a portion of the wash liquor in line 520 can be routed, either directly or indirectly, to oxidation zone 10, as depicted in FIG. 1. Optionally, the wash liquor in line 520 can be concentrated prior to introduction in oxidation zone 10. The optional concentrator can be any device known in the art capable of concentrating the wash liquor stream, such as, for example, membrane separation or evaporation. In another embodiment, at least a portion of the wash liquor in line 520 can be routed to a waste treatment facility.

It will be understood by one skilled in the art that each of the above-described embodiments, as well as any sub-parts of those embodiments, may be operated in a continuous or a non-continuous manner. Non-continuous operations include, but are not limited to, batch-wise operations, cyclical operations, and/or intermittent operations.

In some of the embodiments above, temperature ranges are provided for a specified operation. For each of the above embodiments where a temperature range is provided, the temperature is defined as the average temperature of the substance in the given zone or section. By way of illustration, as discussed above with reference to FIG. 1, a portion of the mother liquor in line 30 can optionally be treated in solids removal zone 32, where solids removal zone 32 can be operated at a temperature in the range of from about 20 to about 195° C. This means that the average temperature of the mother liquor while in solids removal zone 32 can be in the range of from about 20 to about 195° C.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

Definitions

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Claims Not Limited to Disclosed Embodiments

The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A process for producing terephthalic acid and/or isophthalic acid via at least one liquid phase oxidation step of a xylene isomer, that employs a recycled liquid, wherein said recycled liquid comprises at least a portion of a recovered mother liquor that has been recovered downstream of said liquid phase oxidation step, comprising:
   (a) introducing at least a portion of said recovered mother liquor into a purge treatment zone as, wherein said purge feed stream comprises oxidation byproducts from said liquid phase oxidation step and one or more catalyst components, wherein said oxidation byproducts include benzoic acid (BA) and non-BA byproducts; wherein said non-BA byproducts comprise IPA, PA, trimellitic acid, 2,5,4'-tricarboxybiphenyl, 2,5,4'-tricarboxybenzophenone, para-toluic acid (p-TAc), 4-carboxybenzaldehyde (4-CBA), naphthalene dicarboxylic acid, monocarboxyfluorenones, monocarboxyfluorenes, and/or dicarboxyfluorenones;
   (b) separating at least a portion of said purge feed stream into
      (i) a non-BA byproduct rich stream comprising non-BA byproducts and
      (ii) a catalyst and BA rich stream,
   wherein the concentration of said non-BA byproducts in said non-BA byproduct rich stream is at least about 1.5 times the concentration of said non-BA byproducts in said purge feed stream on a weight basis, wherein the cumulative concentration of all of said catalyst components in said catalyst and BA rich stream is at least about 1.5 times the cumulative concentration of all of said catalyst components in said purge feed stream on a weight basis, and wherein the concentration of BA in said catalyst and BA rich stream is at least about 1.5 times the concentration of BA in said purge feed stream on a weight basis; and
   (c) separating at least a portion of said (ii) catalyst and BA rich stream into a catalyst rich stream and a BA rich stream, wherein the cumulative concentration of all of said catalyst components in said catalyst rich stream is at least about 1.5 times the cumulative concentration of all of said catalyst components in said purge feed stream on a weight basis, wherein the concentration of BA in said BA rich stream is at least about 1.5 times the concentration of BA in said purge feed stream on a weight basis;
   wherein a portion of said non-BA byproducts rich stream is subsequently combined with at least one stream containing terephthalic acid and/or isophthalic acid obtained after completion of all liquid phase oxidation to form a combined stream.

2. The process of claim 1, wherein the concentration of said non-BA byproducts in said non-BA byproduct rich stream is at least about 5 times the concentration of said non-BA byproducts in said purge feed stream on a weight basis.

3. The process of claim 1, wherein the cumulative concentration of said non-BA byproducts in said purge feed stream is in the range of from about 500 to about 50,000 ppmw.

4. The process of claim 1, wherein said catalyst components comprise cobalt, manganese, and/or bromine.

5. The process of claim 1, wherein the cumulative concentration of all of said catalyst components in said catalyst rich stream is at least about 5 times the cumulative concentration of all of said catalyst components in said purge feed stream on a weight basis.

6. The process of claim 1, wherein the cumulative concentration of said catalyst components in said purge feed stream is in the range of from about 500 to about 20,000 ppmw.

7. The process of claim 1, wherein the concentration of BA in said BA rich stream is at least about 5 times the concentration of BA in said purge feed stream on a weight basis.

8. The process of claim 1, wherein the concentration of BA in said purge feed stream is in the range of from about 500 to about 150,000 ppmw.

9. The process of claim 1, wherein the cumulative concentration of all of said catalyst components in said catalyst and BA rich stream is at least about 5 times the cumulative concentration of all of said catalyst components in said purge feed stream on a weight basis, and wherein the concentration of BA in said catalyst and BA rich stream is at least about 5 times the concentration of BA in said purge feed stream on a weight basis.

10. The process of claim 1, wherein the concentration of said non-BA byproducts in said non-BA byproduct rich stream is at least about 5 times the concentration of said non-BA byproducts in said purge feed stream on a weight basis, wherein the cumulative concentration of all of said catalyst components in said catalyst rich stream is at least about 5 times the cumulative concentration of all of said catalyst components in said purge feed stream on a weight basis, wherein the concentration of BA in said BA rich stream is at least about 5 times the concentration of BA in said purge feed stream on a weight basis, wherein the cumulative concentration of all of said catalyst components in said catalyst and BA rich stream is at least about 5 times the cumulative concentration of all of said catalyst components in said purge feed stream on a weight basis, and wherein the concentration of BA in said catalyst and BA rich stream is at least about 5 times the concentration of BA in said purge feed stream on a weight basis.

11. The process of claim 1, wherein the concentration of said non-BA byproducts in said purge feed stream is in the range of from about 1,000 to about 20,000 ppmw, wherein the cumulative concentration of said catalyst components in said purge feed stream is in the range of from about 1,000 to about 15,000 ppmw, wherein the concentration of BA in said purge feed stream is in the range of from about 1,000 to about 100,000 ppmw.

12. The process of claim 1, wherein said purge feed stream further comprises at least about 75 weight percent of a solvent.

13. The process of claim 12, wherein said solvent comprises acetic acid and/or water.

14. The process of claim 1, wherein said purge feed stream comprises less than about 5 weight percent solids.

15. The process of claim 1, wherein said catalyst and BA rich stream comprises less than about 5 weight percent solids.

16. The process of claim 1, wherein said non-BA byproduct rich stream is in the form of a wet cake comprising in the range of from about 5 to about 40 weight percent liquid.

17. The process of claim 1, further comprising adding a liquid to said catalyst rich stream thereby producing a reslurried catalyst rich stream.

18. The process of claim 1, wherein said BA rich stream comprises at least about 70 weight percent fluid.

19. The process of claim 1, wherein said separating of step (b) includes removing volatile compounds from said purge feed stream in a concentration section to thereby produce a concentrated stream and thereafter subjecting said concentrated stream to solid/liquid separation in a solid/liquid separation section.

20. The process of claim 19, wherein said concentrated stream comprises in the range of from about 5 to about 70 weight percent solids.

21. The process of claim 19, wherein said solid/liquid separation includes removing a mother liquor from said concentrated stream to produce an initial wet cake and thereafter washing said initial wet cake with a wash feed to thereby produce a washed wet cake.

22. The process of claim 21, wherein said catalyst and BA rich stream comprises at least a portion of the removed mother liquor from said solid/liquid separation section.

23. The process of claim 21, wherein said non-BA byproduct rich stream comprises at least a portion of said washed wet cake from said solid/liquid separation section.

24. The process of claim 1, wherein said separating of step (c) includes removing volatile compounds from said catalyst and BA rich stream in a concentration section to thereby produce a concentrated stream and thereafter treating said concentrated stream in a BA/catalyst separation section.

25. The process of claim 24, wherein said process further comprises separating said concentrated stream into a predominately solid phase stream and a predominately fluid phase stream.

26. The process of claim 25, wherein said BA rich stream comprises at least a portion of said predominately fluid phase stream from said BA/catalyst separation section.

27. The process of claim 25, wherein said catalyst rich stream comprises at least a portion of said predominately solid phase stream from said BA/catalyst separation section.

28. The process of claim 24, wherein said BA/catalyst separation section comprises a dryer.

29. The process of claim 1, wherein said separating of step (c) includes treating said catalyst and BA rich stream in a catalyst removal section to thereby produce a predominately solid phase stream and a predominately fluid phase stream and thereafter subjecting said predominately fluid phase stream to fluid/fluid separation in a BA/solvent separation section.

30. The process of claim 29, wherein said catalyst rich stream comprises at least a portion of said predominately solid phase stream from said catalyst removal section.

31. The process of claim 29, wherein said predominately fluid phase stream comprises a lower volatility portion and a higher volatility portion.

32. The process of claim 31, wherein said fluid/fluid separation comprises substantially separating said lower volatility portion from said higher volatility portion thereby generating a lower volatility stream and a higher volatility stream.

33. The process of claim 32, wherein said BA rich stream comprises at least a portion of said lower volatility stream from said BA/solvent separation section.

34. The process according claim 1 wherein a portion of said combined stream is subsequently used as a feedstock to a polyethylene terephthalate (PET) production process.

* * * * *